US012558438B2

(12) United States Patent
Bradbury et al.

(10) Patent No.: US 12,558,438 B2
(45) Date of Patent: Feb. 24, 2026

(54) IMAGING SYSTEMS AND METHODS FOR PARTICLE-DRIVEN, KNOWLEDGE-BASED, AND PREDICTIVE CANCER RADIOGENOMICS

(71) Applicants: Memorial Sloan Kettering Cancer Center, New York, NY (US); Cornell University, Ithaca, NY (US)

(72) Inventors: Michelle S. Bradbury, New York, NY (US); Cameron Brennan, Haworth, NJ (US); Mithat Gonen, New York, NY (US); Mohan Pauliah, New York, NY (US); Ulrich Wiesner, Ithaca, NY (US)

(73) Assignees: Memorial Sloan Kettering Cancer Center, New York, NY (US); Cornell University, Ithaca, NY (US)

( * ) Notice: Subject to any disclaimer, the term of this patent is extended or adjusted under 35 U.S.C. 154(b) by 794 days.

(21) Appl. No.: 16/315,401

(22) PCT Filed: Jun. 28, 2017

(86) PCT No.: PCT/US2017/039620
§ 371 (c)(1),
(2) Date: Jan. 4, 2019

(87) PCT Pub. No.: WO2018/009379
PCT Pub. Date: Jan. 11, 2018

(65) Prior Publication Data
US 2019/0231903 A1 Aug. 1, 2019

Related U.S. Application Data

(60) Provisional application No. 62/359,684, filed on Jul. 7, 2016.

(51) Int. Cl.
*A61K 49/00* (2006.01)
*A61B 1/00* (2006.01)
(Continued)

(52) U.S. Cl.
CPC .... *A61K 49/0002* (2013.01); *A61B 1/000094* (2022.02); *A61B 5/0035* (2013.01);
(Continued)

(58) Field of Classification Search
CPC ..... G06T 7/0012; A61B 6/5247; A61B 6/481; A61B 6/037; A61B 5/4848; A61B 5/055; A61B 5/0042; A61B 5/0035
See application file for complete search history.

(56) References Cited

U.S. PATENT DOCUMENTS 8,880,146 B1 * 11/2014 Schepkin ............... A61B 5/055
382/131
2005/0215883 A1 9/2005 Hundley et al.
(Continued)

FOREIGN PATENT DOCUMENTS

CN 101001569 A 7/2007
CN 105105697 A 12/2015
(Continued)

OTHER PUBLICATIONS

Yu et al., Potential Utility of Visually AcceSAble Rembrandt Images Assessment in Brain Astrocytoma Grading, Mar./Apr. 2016, Journal of Computer Assisted Tomography, vol. 40, No. 2, pp. 301-306 (Year: 2016).*
(Continued)

*Primary Examiner* — Michael J Carey
*Assistant Examiner* — Zainab Mohammed Aldarraji
(74) *Attorney, Agent, or Firm* — ArentFox Schiff LLP; Daniel W. Clarke

(57) ABSTRACT
Described herein are particle-driven radiogenomics systems and methods that can be used to identify imaging features for prediction of intratumoral and interstitial nanoparticle distributions in cancers (e.g., in low grade and/or high-grade brain cancers (e.g., gliomas, e.g., primary gliomas)). In
(Continued)

certain embodiments, the systems and methods described herein extract and combine quantitative multi-dimensional data generated from structural, functional, and/or metabolic imaging. In certain embodiments, the combined multidimensional data is linked to intratumoral and interstitial nanoparticle distributions. For example, this linked data can be used to determine quantitative functional-metabolic multimodality particle-based imaging features and to predict treatment efficacy. These techniques provide an improved quantitative ability to measure treatment response and determine tumor progressions compared to traditional size-based imaging methods.

34 Claims, 12 Drawing Sheets

(51) Int. Cl.

| | |
|---|---|
| A61B 5/00 | (2006.01) |
| A61B 5/055 | (2006.01) |
| A61B 5/107 | (2006.01) |
| A61B 6/00 | (2006.01) |
| A61B 6/03 | (2006.01) |
| A61B 6/50 | (2024.01) |
| A61K 49/18 | (2006.01) |
| A61K 51/08 | (2006.01) |
| A61K 51/12 | (2006.01) |
| G01R 33/48 | (2006.01) |
| G01R 33/56 | (2006.01) |
| G01R 33/563 | (2006.01) |
| G01T 1/164 | (2006.01) |
| G01T 1/29 | (2006.01) |
| G06T 7/00 | (2017.01) |
| G06T 7/40 | (2017.01) |
| A61B 8/00 | (2006.01) |
| A61B 8/08 | (2006.01) |

(52) U.S. Cl.

CPC ............ *A61B 5/0042* (2013.01); *A61B 5/055* (2013.01); *A61B 5/1072* (2013.01); *A61B 5/1075* (2013.01); *A61B 5/4842* (2013.01); *A61B 5/4848* (2013.01); *A61B 6/03* (2013.01); *A61B 6/037* (2013.01); *A61B 6/481* (2013.01); *A61B 6/501* (2013.01); *A61B 6/5217* (2013.01); *A61B 6/5247* (2013.01); *A61K 49/1818* (2013.01); *A61K 51/082* (2013.01); *A61K 51/088* (2013.01); *A61K 51/1244* (2013.01); *G01R 33/481* (2013.01); *G01R 33/4812* (2013.01); *G01R 33/4814* (2013.01); *G01R 33/5601* (2013.01); *G01R 33/56341* (2013.01); *G01T 1/1642* (2013.01); *G01T 1/2985* (2013.01); *G06T 7/0012* (2013.01); *G06T 7/40* (2013.01); *A61B 6/4417* (2013.01); *A61B 8/085* (2013.01); *A61B 8/4416* (2013.01); *A61B 8/481* (2013.01); *A61B 8/5223* (2013.01); *A61B 8/5261* (2013.01); *G06T 2207/10072* (2013.01); *G06T 2207/10088* (2013.01); *G06T 2207/30096* (2013.01)

(56) References Cited

U.S. PATENT DOCUMENTS

| | | | |
|---|---|---|---|
| 2012/0035458 A1 | 2/2012 | Flynn | |
| 2012/0121515 A1* | 5/2012 | Dang ................... | G01N 33/574 424/9.1 |
| 2013/0039848 A1 | 2/2013 | Bradbury et al. | |
| 2014/0248210 A1* | 9/2014 | Bradbury ........... | A61K 51/1244 424/9.4 |
| 2015/0182118 A1* | 7/2015 | Bradbury .................. | A61P 9/00 600/431 |
| 2015/0343091 A1 | 12/2015 | Yoo et al. | |
| 2015/0381909 A1* | 12/2015 | Butte ................... | A61B 1/0638 250/578.1 |
| 2016/0129131 A1 | 5/2016 | Vitari et al. | |
| 2017/0020816 A1* | 1/2017 | Nagy ................... | A61K 9/1271 |
| 2017/0192291 A1 | 7/2017 | Shi | |

FOREIGN PATENT DOCUMENTS

| | | | |
|---|---|---|---|
| CN | 105263390 A | 1/2016 | |
| EP | 2314218 A1 | 4/2011 | |
| EP | 2968621 B1 | 8/2022 | |
| WO | WO-2014/130736 A1 | 8/2014 | |
| WO | WO-2014/145606 A1 | 9/2014 | |
| WO | WO-2014/176375 A2 | 10/2014 | |
| WO | WO-2015/103420 A1 | 7/2015 | |
| WO | WO-2015138385 A1 * | 9/2015 | ........... A61B 5/0263 |
| WO | WO-2016/26434 A1 | 2/2016 | |
| WO | WO-2016/100340 A1 | 6/2016 | |
| WO | WO-2016/164578 A1 | 10/2016 | |
| WO | WO-2017/106525 A1 | 6/2017 | |
| WO | WO-2017/189961 A1 | 11/2017 | |
| WO | WO-2018/009379 A1 | 1/2018 | |

OTHER PUBLICATIONS

Li et al., MRI Tissue Classification and Bias Field Estimation Based on Coherent Local Intensity Clustering: A Unified Energy Minimization Framework, 2009, Information Processing in Medical Imaging, vol. 5636, pp. 288-299 (Year: 2009).*

Kim et al., Gliomas: Application of Cumulative Histogram Analysis of Normalized Cerebral Blood Volume on 3T MRI to Tumor Grading, 2013, PLoS One, vol. 8, issue 5, pp. 1-11 (Year: 2013).*

Liu, H. et al., Application of iron oxide nanoparticles in glioma imaging and therapy: from bench to bedside, Nanoscale, 8(15):7808-7826, (2016).

Mandeville, Joseph B., Iron fMRI measurements of CBV and implications for BOLD signal, Neuroimage, Elsevier, Amsterdam, NL, 62(2):1000-1008, XP028502194, (2012).

Na, H. Y.et al., Inorganic Nanoparticles for MRI Contrast Agents, Advanced Materials, 21(21):2133-2148, XP055251674, (2009).

Phillips, E. et al., Clinical translation of an ultrasmall inorganic optical-PET imaging nanoparticle probe, Science Translational Medicine, 6(260):260ra149-260ra149, (2014).

Tran, L., et al., High-dimensional MRI data analysis using a large-scale manifold learning approach, Machine Vision and Applications, Springer Verlag, DE, 24(5):995-1014, (2013).

Wilks, M. Q., et al., Imaging PEG-Like Nanoprobes in Tumor, Transient Ischemia, and Inflammatory Disease Models, Bioconjugate Chemistry, 26(6):1061-1069, XP055283192, (2015).

Brat, D. J. et al., Comprehensive, Integrative Genomic Analysis of Diffuse Lower-Grade Gliomas, New England Journal of Medicine, 372:2481-2498, (2015).

Dang, L. et al., Cancer-associated IDH1 mutations produce 2-hydroxyglutarate, Nature, 462(7274):739-744, (2009).

Detappe, A. et al., Advanced multimodal nanoparticles delay tumor progression with clinical radiation therapy, Journal of Controlled Release, 238:103-113 (2016).

Hilderbrand, Scott and Weissleder, Ralph, Near-infrared fluorescence: application to in vivo molecular imaging, Current Opinion in Chemical Biology, 14:71-9, 2010.

International Search Report, PCT/US2017/39620, (Imaging Systems and Methods for Particle-Driven, Knowledge-Based, and Predictive Cancer Radiogenomics filed Jun. 28, 2017) issued by ISA/US, 3 pages (Sep. 15, 2017).

Van den Bent, M. J. et al., Response assessment in neuro-oncology (a report of the RANO group): assessment of outcome in trials of diffuse low-grade gliomas. The lancet oncology, 12:583-593, (2011).

(56)  References Cited

OTHER PUBLICATIONS

Ward, P. S. et al., Identification of additional IDH mutations associated with oncometabolite R(–)-2-hydroxyglutarate production, Oncogene, 31(19):2491-2498. (2012).

Wen, P. Y. et al., Updated Response Assessment Criteria for High-Grade Gliomas: Response Assessment in Neuro-Oncology Working Group, Journal of Clinical Oncology, 28:1963-1972, (2010).

Written Opinion, PCT/US2017/39620, (Imaging Systems and Methods for Particle-Driven, Knowledge-Based, and Predictive Cancer Radiogenomics filed Jun. 28, 2017) issued by ISA/US, 3 pages (Sep. 15, 2017).

* cited by examiner

FLAIR                Segmented                Voxel-wise
                                              Confidence

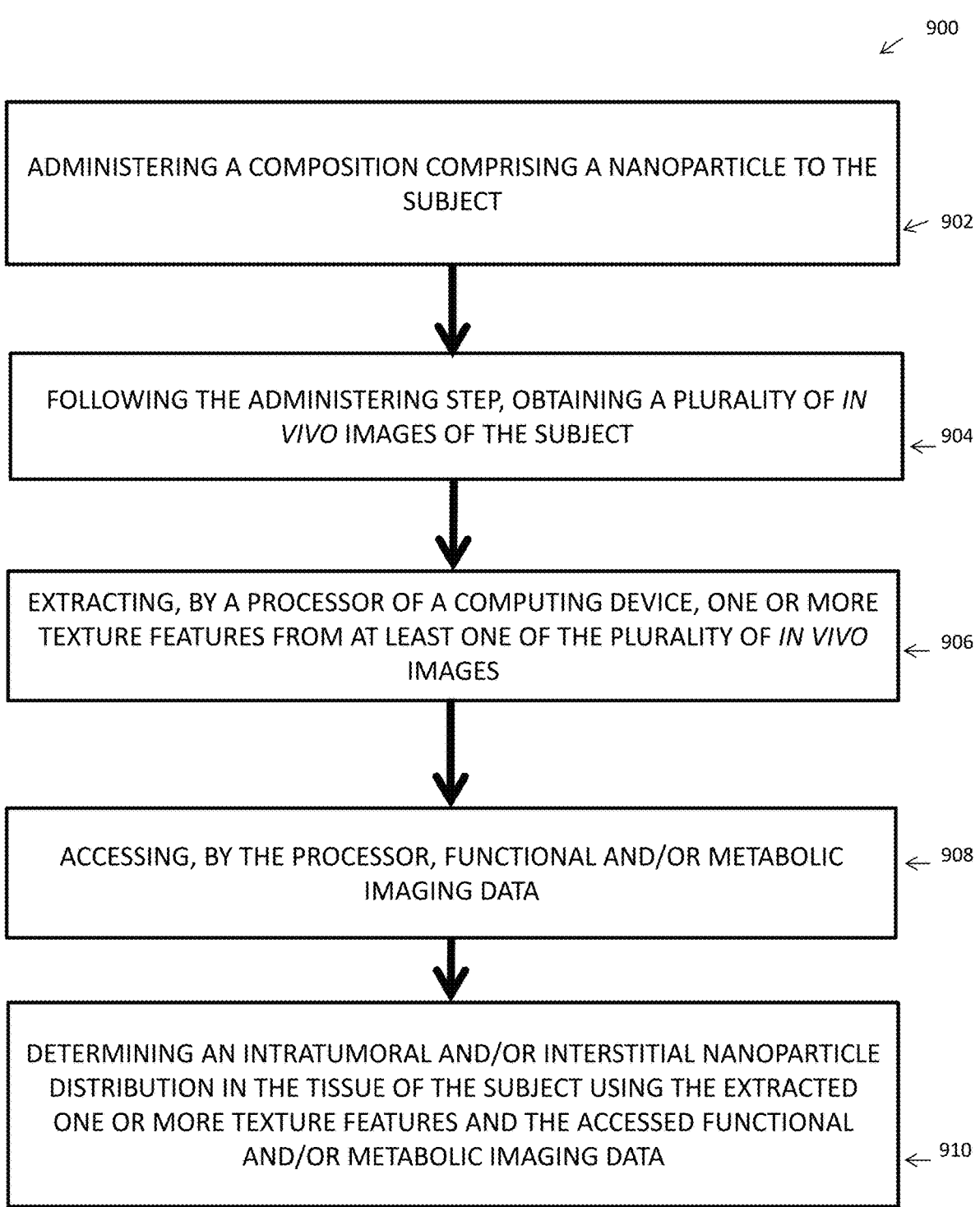

900

ADMINISTERING A COMPOSITION COMPRISING A NANOPARTICLE TO THE SUBJECT

902

FOLLOWING THE ADMINISTERING STEP, OBTAINING A PLURALITY OF *IN VIVO* IMAGES OF THE SUBJECT

904

EXTRACTING, BY A PROCESSOR OF A COMPUTING DEVICE, ONE OR MORE TEXTURE FEATURES FROM AT LEAST ONE OF THE PLURALITY OF *IN VIVO* IMAGES

906

ACCESSING, BY THE PROCESSOR, FUNCTIONAL AND/OR METABOLIC IMAGING DATA

908

DETERMINING AN INTRATUMORAL AND/OR INTERSTITIAL NANOPARTICLE DISTRIBUTION IN THE TISSUE OF THE SUBJECT USING THE EXTRACTED ONE OR MORE TEXTURE FEATURES AND THE ACCESSED FUNCTIONAL AND/OR METABOLIC IMAGING DATA

IMAGING SYSTEMS AND METHODS FOR PARTICLE-DRIVEN, KNOWLEDGE-BASED, AND PREDICTIVE CANCER RADIOGENOMICS

CROSS REFERENCE TO RELATED APPLICATION

The application claims the benefit of U.S. Application Ser. No. 62/359,684 filed on Jul. 7, 2016, the disclosure of which is hereby incorporated by reference in its entirety.

GOVERNMENT SUPPORT

This invention was made with government support under grant number CA199081 awarded by National Institutes of Health (NIH). The government has certain rights in the invention.

FIELD OF THE INVENTION

The invention relates generally to systems and methods for medical imaging and analysis of image data. More particularly, in certain embodiments, the invention relates to techniques combining structural, functional, and/or metabolic image analysis approaches with the use of nanoparticle-based species.

BACKGROUND

Human cancers exhibit strong intra- and inter-patient heterogeneity. These differences occur at different spatial scales such as molecular-genetic, cellular (e.g., tumor/microenvironment), whole tissues, and organs. As a result, much of the discussion of precision medicine has focused on molecular characterization using genomic and proteomic technologies.

Radiogenomics analysis alone has revealed that, for instance, prognostic radiomic signatures capturing intratumoral heterogeneity are associated with underlying gene-expression patterns for specific tumor types. Over the past decade, the use and role of such tools have expanded in clinical oncology from primarily diagnostic tools to tools that play a more central role in the context of individualized medicine. These technologies can be used individually or in combination, depending on the biological/clinical question(s) of interest to monitor development and progression of disease, assess prognosis, guide therapy, and/or predict therapeutic response and/or efficacy.

However, current technologies in radiogenomics suffer from size-dependent limitations of delivery/transport. For example, the standard of care for evaluating the efficacy of drugs tested in clinical trials remain dependent on the size of the tumor despite the increasing recognition that changes in tumor size may inaccurately reflect differences in tumor biology, especially for cases where tumors that are treated with non-cytotoxic treatments.

To account for differences in tumor size, technologies such as diffusion imaging (e.g., diffusion weighted imaging (DWI), e.g., diffusion tensor imaging (DTI)) have attempted to provide measurements of water diffusion, anisotropy, and cellularity. Moreover, technologies such as perfusion imaging (e.g., dynamic contrast enhanced (DCE)) have attempted to provide measurements of leakiness (Ktrans) and microvascular perfusion (plasma volume, VP). Each of these techniques can provide independent characterizations of tumor diffusion, cellularity, leakiness, perfusion and heterogeneity. However, as tumors are spatially and temporally heterogeneous, the use of these techniques as part of biopsy-based molecular assays is limited, and underscores the need for complementary advanced non-invasive imaging tools, both within and across tumors.

Advances in genome-wide technology have identified three molecular classes of low-grade gliomas that have superior correlations to outcomes than histologic grades. Of these classes, isocitrate dehydrogenase (IDH) mutations represent a particularly compelling target for precision imaging and therapy. Mutations in the IDH enzyme are the most common genetic alterations in World Health Organization Grade (WHO) grade II/III human gliomas. IDH mutations result in the neomorphic activity of the enzyme to produce the oncometabolite R-2-hydroxyglutarate (2HG). 2HG accumulates in IDH mutant gliomas and competitively inhibits a family of more than fifty $\alpha$-ketoglutarate dependent enzymes, including many enzymes involved in gene regulation and cellular differentiation.

Many therapies can cause treatment-induced and/or immune-mediated reactions as part of their anti-tumor activity. Further, although the standard of care scans can routinely include diffusion and perfusion imaging, the analysis of these functional data continues to rely upon qualitative visual analysis by an expert neuroradiologist.

Thus, there remains a need for tools to more accurately quantify treatment response and tumor progression than current size-based criteria.

SUMMARY

Described herein are particle-driven radiogenomics systems and methods that can be used, for example, to identify imaging features for prediction of intratumoral and interstitial nanoparticle distributions in the tissue of a subject (e.g., in a metastatic disease that goes to the brain, e.g., in low grade and/or high-grade brain cancers (e.g., gliomas)). The nanoparticles may have cancer-targeting ligands and/or therapeutics attached thereto and may be administered for in vivo imaging/tracking. In certain embodiments, the systems and methods described herein extract and combine quantitative multi-dimensional data generated from structural, functional, and/or metabolic imaging techniques. In certain embodiments, the combined multidimensional data is linked to intratumoral and interstitial nanoparticle distributions. For example, this linked data can be used to determine quantitative functional-metabolic multimodality particle-based imaging features and to predict treatment efficacy.

Systems and methods described herein include the following techniques: (1) particle-driven (versus molecularly-driven) radiomics; (2) fusion of structural with functional (and metabolic) imaging data sets; (3) structural imaging techniques beyond texture analysis, and (4) extraction of robust imaging features derived from molecular therapeutic experiments to determine treatment efficacy (e.g., as inhibitors are attached to particle probes). These techniques provide an improved quantitative ability to measure treatment response and determine tumor progressions compared to traditional size-based imaging methods.

Exemplary quantitative imaging features that can be extracted through radiomics include textural features, functional parameters, and clusters of features from multiparametric imaging. Radiogenomic analyses define relationships (e.g., association maps) between such imaging features and molecular markers (omics), thus establishing a connection between diagnostic imaging and molecular diagnostics.

Particle-driven radiogenomics identifies key prognostic imaging features, better understands tumor heterogeneity and treatment response, and guides molecularly-driven biopsies. Accordingly, particle-driven radiogenomics provides complementary and interchangeable information relative to other sources (e.g., demographics, pathology, blood biomarkers, or genomics), which improves upon conventional individualized treatment selection and monitoring. Further, the systems and methods described herein can have large clinical impact at low cost.

In one aspect, the invention is directed to an in vivo method for determining intratumoral and/or interstitial nanoparticle distribution in a tissue of a subject, the method comprising the steps of: administering a composition comprising a nanoparticle to the subject (e.g., wherein "nanoparticle" means a plurality of individual nanoparticles of the same or different type) (e.g., wherein the nanoparticle has average diameter no greater than 20 nm, e.g., no greater than 15 nm, e.g., no greater than 10 nm, e.g., between 1 and 10 nm, e.g., between 3 and 8 nm) (e.g., wherein the nanoparticle is dual-modality cRGDY-PEG-C' dots); following the administering step, obtaining a plurality of in vivo images of the subject; extracting, by a processor of a computing device, one or more texture features from at least one of the plurality of in vivo images; accessing, by the processor, functional and/or metabolic imaging data (e.g., from at least one of the plurality of in vivo images); and determining an intratumoral and/or interstitial nanoparticle distribution in the tissue of the subject using the extracted one or more texture features and the accessed functional and/or metabolic imaging data.

In another aspect, the invention is directed to a method for identifying texture features to predict treatment efficacy in a tissue (of a subject, the method comprising the steps of: administering a composition comprising a nanoparticle to the subject (e.g., wherein "nanoparticle" means a plurality of individual nanoparticles of the same or different type) (e.g., wherein the nanoparticle has average diameter no greater than 20 nm, e.g., no greater than 15 nm, e.g., no greater than 10 nm, e.g., between 1 and 10 nm, e.g., between 3 and 8 nm); following the administering step, obtaining one or more in vivo images of the subject; extracting, by a processor of a computing device, one or more features from at least one of the plurality of in vivo images; and determining (e.g., by the processor) a measure of treatment efficacy using the extracted one or more features.

In another aspect, the invention is directed to a method for evaluating glioma heterogeneity, the method comprising the steps of: administering a composition comprising a nanoparticle to the subject (e.g., wherein "nanoparticle" means a plurality of individual nanoparticles of the same or different type) (e.g., wherein the nanoparticle has average diameter no greater than 20 nm, e.g., no greater than 15 nm, e.g., no greater than 10 nm, e.g., between 1 and 10 nm, e.g., between 3 and 8 nm); following the administering step, obtaining one or more in vivo images of the subject; extracting, by a processor of a computing device, one or more features from at least one of the plurality of in vivo images; and determining (e.g., by the processor) a measure of glioma heterogeneity using the extracted one or more features.

In certain embodiments, the tissue comprises a metastatic disease that goes to the brain. In certain embodiments, the tissue comprises a primary glioma. In certain embodiments, the tissue comprises a low-grade glioma or high-grade glioma.

In certain embodiments, the nanoparticle has an average diameter no greater than 20 nm.

In certain embodiments, a radioisotope (e.g., a positron emission tomography (PET) tracer) is attached directly or indirectly to the nanoparticle.

In certain embodiments, a therapeutic is attached directly or indirectly to the nanoparticle.

In certain embodiments, the plurality of in vivo images comprises a member selected from the group consisting of a positron emission tomography (PET) images(s), x-ray images(s), magnetic resonance imaging (MRI) images(s), Computed Tomography (CT) images(s), Single-Photon Emission Computed Tomography (SPECT) images(s), PET-CT images(s), and ultrasound image(s). In certain embodiments, the plurality of in vivo images comprises a combination of two or more of PET images(s), x-ray images(s), MRI images(s), CT images(s), SPECT images(s), PET-CT images(s), and ultrasound image(s). In certain embodiments, the one or more texture features comprise Gabor edge features and/or Visually Accessible Rembrandt features. In certain embodiments, the functional and/or metabolic imaging data comprises one or more of the following: diffusion-weighted imaging data, diffusion tensor imaging data, and/or dynamic contrast enhanced T1 perfusion imaging data. In certain embodiments, the texture features comprise quantitative functional MR texture features.

In certain embodiments, a molecular inhibitor is attached directly or indirectly to the nanoparticle.

In certain embodiments, the one or more features are functional and/or structural features.

In certain embodiments, the extracting step identifies quantitative functional magnetic resonance (MR) texture features.

In certain embodiments, a molecular inhibitor is attached to the nanoparticle, and wherein the measure is a prediction of treatment efficacy in a low-grade glioma treated with the mutation specific inhibitor therapy.

In certain embodiments, the determining step uses high-dimensional data from one or more radiomic analysis of MR diffusion and/or perfusion functional images to predict inhibitor treatment efficacy (e.g., in metastatic diseases that goes to the brain, e.g., in gliomas, e.g., in primary gliomas, e.g., in high-grade gliomas, e.g., in low-grade gliomas, e.g., in IDH mutant gliomas). In certain embodiments, the determining step uses the extracted one or more features in addition to data regarding genetic mutations and/or disease history of the subject.

In certain embodiments, the method further comprises identifying an MR vascular signature.

In certain embodiments, the obtaining step comprises producing a multi-parametric map (e.g., PET/CT, DCE-MRI, or MM).

In certain embodiments, the extracting step comprises determining a multi-level overall minimizing energy criteria for characterization.

In certain embodiments, the determining step comprises determining hemodynamic metrics in comparison with contralateral using a computation of the number of interface junctions inside a tumor region.

In certain embodiments, the determining step comprises determining an MR vascular signature.

In another aspect, the invention is directed to a system comprising: a nanoparticle (e.g., wherein "nanoparticle" means a plurality of individual nanoparticles of the same or different type) (e.g., wherein the nanoparticle has average diameter no greater than 20 nm, e.g., no greater than 15 nm, e.g., no greater than 10 nm, e.g., between 1 and 10 nm, e.g., between 3 and 8 nm) (e.g., wherein a radioisotope (e.g., PET tracer) is attached directly or indirectly to the nanoparticle) (e.g., wherein a therapeutic is attached directly or indirectly to the nanoparticle) (e.g., wherein the nanoparticle is dual-modality cRGDY-PEG-C' dots); one or more imaging device(s) (e.g., MR, PET, SPECT, CT, ultrasound, X-ray, and/or a combination thereof); a processor; and a nontransitory computer readable medium having instructions stored thereon, wherein the instructions, when executed by the processor, cause the processor to: (i) extract one or more texture features from at least one of a plurality of in vivo images obtained using the one or more imaging device(s) (e.g., Gabor edge features and/or Visually Accessible Rembrandt features); (ii) access functional and/or metabolic imaging data from at least one of the plurality of in vivo images (e.g., wherein the functional and/or metabolic imaging data comprises one or more of the following: diffusion-weighted imaging data, diffusion tensor imaging data, and/or dynamic contrast enhanced T1 perfusion imaging data); (iii) determine an intratumoral and/or interstitial nanoparticle distribution in the tissue (e.g., glioma) of the subject using the extracted one or more texture features and the accessed functional and/or metabolic imaging data; and (iv) cause display of a graphical representation of the intratumoral and/or interstitial nanoparticle distribution in the tissue (e.g., superimposed on an image of the tissue captured by the one or more imaging devices, e.g., still or video images, e.g., presented in real time or near real-time).

In another aspect, the invention is directed to a system comprising: a nanoparticle (e.g., wherein "nanoparticle" means a plurality of individual nanoparticles of the same or different type) (e.g., wherein the nanoparticle has average diameter no greater than 20 nm, e.g., no greater than 15 nm, e.g., no greater than 10 nm, e.g., between 1 and 10 nm, e.g., between 3 and 8 nm) (e.g., wherein a radioisotope (e.g., PET tracer) is attached directly or indirectly to the nanoparticle) (e.g., wherein a therapeutic is attached directly or indirectly to the nanoparticle) (e.g., wherein the nanoparticle is dual-modality cRGDY-PEG-C' dots); one or more imaging device(s) (e.g., MR, PET, SPECT, CT, ultrasound, X-ray, and/or a combination thereof); a processor; and a nontransitory computer readable medium having instructions stored thereon, wherein the instructions, when executed by the processor, cause the processor to: (i) extract one or more features (e.g., functional and/or structural features) from at least one of the plurality of in vivo images (e.g., identify quantitative functional magnetic resonance (MR) texture features); (ii) determine a measure of treatment efficacy using the extracted one or more features (e.g., wherein a molecular inhibitor is attached to the nanoparticle and wherein the measure is a prediction of treatment efficacy in a low-grade glioma treated with the mutation specific inhibitor therapy) (e.g., wherein the determining step uses high-dimensional data from one or more radiomic analysis of MR diffusion and/or perfusion functional images to predict inhibitor treatment efficacy (e.g., in IDH mutant gliomas)) (e.g., wherein the determining step uses the extracted one or more features in addition to data regarding genetic mutations and/or disease history of the subject); and (iii) cause display of a graphical representation of the intratumoral and/or interstitial nanoparticle distribution in the tissue (e.g., superimposed on an image of the tissue captured by the one or more imaging devices, e.g., still or video images, e.g., presented in real time or near real-time).

In another aspect, the invention is directed to a system comprising: a nanoparticle (e.g., wherein "nanoparticle" means a plurality of individual nanoparticles of the same or different type) (e.g., wherein the nanoparticle has average diameter no greater than 20 nm, e.g., no greater than 15 nm, e.g., no greater than 10 nm, e.g., between 1 and 10 nm, e.g., between 3 and 8 nm) (e.g., wherein a radioisotope (e.g., PET tracer) is attached directly or indirectly to the nanoparticle) (e.g., wherein a therapeutic is attached directly or indirectly to the nanoparticle) (e.g., wherein the nanoparticle is dual-modality cRGDY-PEG-C' dots); one or more imaging device(s) (e.g., MR, PET, SPECT, CT, ultrasound, X-ray, and/or a combination thereof); a processor; and a nontransitory computer readable medium having instructions stored thereon, wherein the instructions, when executed by the processor, cause the processor to: (i) extract one or more features (e.g., functional and/or structural features) from at least one of the plurality of in vivo images (e.g., determine a multi-level overall minimizing energy criteria for characterization); (ii) determine a measure of glioma heterogeneity using the extracted one or more features (e.g., determine hemodynamic metrics in comparison with contralateral using a computation of the number of interface junctions inside a tumor region) (e.g., determine an MR vascular signature); and (iii) cause display of a graphical representation of the intratumoral and/or interstitial nanoparticle distribution in the tissue (e.g., superimposed on an image of the tissue captured by the one or more imaging devices, e.g., still or video images, e.g., presented in real time or near real-time).

Elements of embodiments involving one aspect of the invention (e.g., methods) can be applied in embodiments involving other aspects of the invention (e.g., systems), and vice versa.

Definitions

In order for the present disclosure to be more readily understood, certain terms are first defined below. Additional definitions for the following terms and other terms are set forth throughout the specification.

In this application, the use of "or" means "and/or" unless stated otherwise. As used in this application, the term "comprise" and variations of the term, such as "comprising" and "comprises," are not intended to exclude other additives, components, integers or steps. As used in this application, the terms "about" and "approximately" are used as equivalents. Any numerals used in this application with or without about/approximately are meant to cover any normal fluctuations appreciated by one of ordinary skill in the relevant art. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

"Administration": The term "administration" refers to introducing a substance into a subject. In general, any route of administration may be utilized including, for example, parenteral (e.g., intravenous), oral, topical, subcutaneous, peritoneal, intraarterial, inhalation, vaginal, rectal, nasal, introduction into the cerebrospinal fluid, or instillation into body compartments. In certain embodiments, administration is oral. Additionally or alternatively, in certain embodiments, administration is parenteral. In certain embodiments, administration is intravenous.

"Antibody": As used herein, the term "antibody" refers to a polypeptide that includes canonical immunoglobulin sequence elements sufficient to confer specific binding to a particular target antigen. Intact antibodies as produced in nature are approximately 150 kD tetrameric agents comprised of two identical heavy chain polypeptides (about 50 kD each) and two identical light chain polypeptides (about 25 kD each) that associate with each other into what is commonly referred to as a "Y-shaped" structure. Each heavy chain is comprised of at least four domains (each about 110 amino acids long)—an amino-terminal variable (VH) domain (located at the tips of the Y structure), followed by three constant domains: $CH_1$, $CH_2$, and the carboxy-terminal $CH_3$ (located at the base of the Y's stem). A short region, known as the "switch", connects the heavy chain variable and constant regions. The "hinge" connects $CH_2$ and $CH_3$ domains to the rest of the antibody. Two disulfide bonds in this hinge region connect the two heavy chain polypeptides to one another in an intact antibody. Each light chain is comprised of two domains—an amino-terminal variable (VL) domain, followed by a carboxy-terminal constant (CL) domain, separated from one another by another "switch". Intact antibody tetramers are comprised of two heavy chain-light chain dimers in which the heavy and light chains are linked to one another by a single disulfide bond; two other disulfide bonds connect the heavy chain hinge regions to one another, so that the dimers are connected to one another and the tetramer is formed. Naturally-produced antibodies are also glycosylated, typically on the $CH_2$ domain. Each domain in a natural antibody has a structure characterized by an "immunoglobulin fold" formed from two beta sheets (e.g., 3-, 4-, or 5-stranded sheets) packed against each other in a compressed antiparallel beta barrel. Each variable domain contains three hypervariable loops known as "complement determining regions" (CDR1, CDR2, and CDR3) and four somewhat invariant "framework" regions (FR1, FR2, FR3, and FR4). When natural antibodies fold, the FR regions form the beta sheets that provide the structural framework for the domains, and the CDR loop regions from both the heavy and light chains are brought together in three-dimensional space so that they create a single hypervariable antigen binding site located at the tip of the Y structure. The Fc region of naturally-occurring antibodies binds to elements of the complement system, and also to receptors on effector cells, including for example effector cells that mediate cytotoxicity. Affinity and/or other binding attributes of Fc regions for Fc receptors can be modulated through glycosylation or other modification. In certain embodiments, antibodies produced and/or utilized in accordance with the present invention include glycosylated Fc domains, including Fc domains with modified or engineered such glycosylation. For purposes of the present invention, in certain embodiments, any polypeptide or complex of polypeptides that includes sufficient immunoglobulin domain sequences as found in natural antibodies can be referred to and/or used as an "antibody", whether such polypeptide is naturally produced (e.g., generated by an organism reacting to an antigen), or produced by recombinant engineering, chemical synthesis, or other artificial system or methodology. In certain embodiments, an antibody is polyclonal; in certain embodiments, an antibody is monoclonal. In certain embodiments, an antibody has constant region sequences that are characteristic of mouse, rabbit, primate, or human antibodies. In certain embodiments, antibody sequence elements are humanized, primatized, chimeric, etc, as is known in the art. Moreover, the term "antibody" as used herein, can refer in appropriate embodiments (unless otherwise stated or clear from context) to any of the art-known or developed constructs or formats for utilizing antibody structural and functional features in alternative presentation. For example, embodiments, an antibody utilized in accordance with the present invention is in a format selected from, but not limited to, intact IgG, IgE and IgM, bi- or multi-specific antibodies (e.g., Zybodies®, etc), single chain Fvs, polypeptide-Fc fusions, Fabs, cameloid antibodies, masked antibodies (e.g., Probodies®), Small Modular ImmunoPharmaceuticals ("SMIPs™"), single chain or Tandem diabodies (TandAb®), VHHs Anticalins®, Nanobodies®, minibodies, BiTE®s, ankyrin repeat proteins or DARPINs®, Avimers®, a DART, a TCR-like antibody, Adnectins®, Affilins®, Trans-Bodies®, Affibodies®, a TrimerX®, MicroProteins, Fynomers®, Centyrins®, and a KALBITOR®. In certain embodiments, an antibody may lack a covalent modification (e.g., attachment of a glycan) that it would have if produced naturally. In certain embodiments, an antibody may contain a covalent modification (e.g., attachment of a glycan, a payload [e.g., a detectable moiety, a therapeutic moiety, a catalytic moiety, etc], or other pendant group [e.g., polyethylene glycol, etc.]).

"Antibody fragment": As used herein, an "antibody fragment" includes a portion of an intact antibody, such as, for example, the antigen-binding or variable region of an antibody. Examples of antibody fragments include Fab, Fab', F(ab')2, and Fv fragments; triabodies; tetrabodies; linear antibodies; single-chain antibody molecules; and multi specific antibodies formed from antibody fragments. For example, antibody fragments include isolated fragments, "Fv" fragments, consisting of the variable regions of the heavy and light chains, recombinant single chain polypeptide molecules in which light and heavy chain variable regions are connected by a peptide linker ("ScFv proteins"), and minimal recognition units consisting of the amino acid residues that mimic the hypervariable region. In many embodiments, an antibody fragment contains sufficient sequence of the parent antibody of which it is a fragment that it binds to the same antigen as does the parent antibody; in certain embodiments, a fragment binds to the antigen with a comparable affinity to that of the parent antibody and/or competes with the parent antibody for binding to the antigen. Examples of antigen binding fragments of an antibody include, but are not limited to, Fab fragment, Fab' fragment, F(ab')2 fragment, scFv fragment, Fv fragment, dsFv diabody, dAb fragment, Fd' fragment, Fd fragment, and an isolated complementarity determining region (CDR) region. An antigen binding fragment of an antibody may be produced by any means. For example, an antigen binding fragment of an antibody may be enzymatically or chemically produced by fragmentation of an intact antibody and/or it may be recombinantly produced from a gene encoding the partial antibody sequence. Alternatively or additionally, antigen binding fragment of an antibody may be wholly or partially synthetically produced. An antigen binding fragment of an antibody may optionally comprise a single chain antibody fragment. Alternatively or additionally, an antigen binding fragment of an antibody may comprise multiple chains which are linked together, for example, by disulfide linkages. An antigen binding fragment of an antibody may optionally comprise a multimolecular complex. A functional single domain antibody fragment is in a range from about 5 kDa to about 25 kDa, e.g., from about 10 kDa to about 20 kDa, e.g., about 15 kDa; a functional single-chain fragment is from about 10 kDa to about 50 kDa, e.g., from about 20 kDa to about 45 kDa, e.g., about 25 kDa to about 30 kDa; and a functional fab fragment is from about 40 kDa to about 80 kDa, e.g., from about 50 kDa to about 70 kDa, e.g., about 60 kDa.

"Associated": As used herein, the term "associated" typically refers to two or more entities in physical proximity with one another, either directly or indirectly (e.g., via one or more additional entities that serve as a linking agent), to form a structure that is sufficiently stable so that the entities remain in physical proximity under relevant conditions, e.g., physiological conditions. In some embodiments, associated moieties are covalently linked to one another. In some embodiments, associated entities are non-covalently linked. In some embodiments, associated entities are linked to one another by specific non-covalent interactions (i.e., by interactions between interacting ligands that discriminate between their interaction partner and other entities present in the context of use, such as, for example. streptavidin/avidin interactions, antibody/antigen interactions, etc.). Alternatively or additionally, a sufficient number of weaker non-covalent interactions can provide sufficient stability for moieties to remain associated. Exemplary non-covalent interactions include, but are not limited to, electrostatic interactions, hydrogen bonding, affinity, metal coordination, physical adsorption, host-guest interactions, hydrophobic interactions, pi stacking interactions, van der Waals interactions, magnetic interactions, electrostatic interactions, dipole-dipole interactions, etc.

"Agent": The term "agent" refers to a compound or entity of any chemical class including, for example, polypeptides, nucleic acids, saccharides, lipids, small molecules, metals, or combinations thereof. As will be clear from context, in some embodiments, an agent can be or comprise a cell or organism, or a fraction, extract, or component thereof. In some embodiments, an agent is or comprises a natural product in that it is found in and/or is obtained from nature. In some embodiments, an agent is or comprises one or more entities that are man-made in that it is designed, engineered, and/or produced through action of the hand of man and/or are not found in nature. In some embodiments, an agent may be utilized in isolated or pure form; in some embodiments, an agent may be utilized in crude form. In some embodiments, potential agents are provided as collections or libraries, for example that may be screened to identify or characterize active agents within them. Some particular embodiments of agents that may be utilized include small molecules, antibodies, antibody fragments, aptamers, siRNAs, shRNAs, DNA/RNA hybrids, antisense oligonucleotides, ribozymes, peptides, peptide mimetics, peptide nucleic acids, small molecules, etc. In some embodiments, an agent is or comprises a polymer. In some embodiments, an agent contains at least one polymeric moiety. In some embodiments, an agent comprises a therapeutic, diagnostic and/or drug.

"Biocompatible": The term "biocompatible", as used herein is intended to describe materials that do not elicit a substantial detrimental response in vivo. In certain embodiments, the materials are "biocompatible" if they are not toxic to cells. In certain embodiments, materials are "biocompatible" if their addition to cells in vitro results in less than or equal to 20% cell death, and/or their administration in vivo does not induce inflammation or other such adverse effects. In certain embodiments, materials are biodegradable.

"Biodegradable": As used herein, "biodegradable" materials are those that, when introduced into cells, are broken down by cellular machinery (e.g., enzymatic degradation) or by hydrolysis into components that cells can either reuse or dispose of without significant toxic effects on the cells. In certain embodiments, components generated by breakdown of a biodegradable material do not induce inflammation and/or other adverse effects in vivo. In certain embodiments, biodegradable materials are enzymatically broken down. Alternatively or additionally, in certain embodiments, biodegradable materials are broken down by hydrolysis. In certain embodiments, biodegradable polymeric materials break down into their component polymers. In certain embodiments, breakdown of biodegradable materials (including, for example, biodegradable polymeric materials) includes hydrolysis of ester bonds. In certain embodiments, breakdown of materials (including, for example, biodegradable polymeric materials) includes cleavage of urethane linkages.

"Cancer": As used herein, the term "cancer" refers to a malignant neoplasm or tumor (Stedman's Medical Dictionary, 25th ed.; Hensly ed.; Williams & Wilkins: Philadelphia, 1990). Exemplary cancers include, but are not limited to, brain cancer (e.g., meningioma, glioblastomas, glioma (e.g., astrocytoma, oligodendroglioma), medulloblastoma), prostate cancer, melanoma, breast cancer, gynecological malignancies, colorectal cancers.

"Carrier": As used herein, "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin.

"Detector": As used herein, the term "detector" includes any detector of electromagnetic radiation including, but not limited to, CCD camera, photomultiplier tubes, photodiodes, and avalanche photodiodes.

"In vitro": The term "in vitro" as used herein refers to events that occur in an artificial environment, e.g., in a test tube or reaction vessel, in cell culture, etc., rather than within a multi-cellular organism.

"In vivo": As used herein "in vivo" refers to events that occur within a multi-cellular organism, such as a human and a non-human animal. In the context of cell-based systems, the term may be used to refer to events that occur within a living cell (as opposed to, for example, in vitro systems).

"Imaging agent": The term "imaging agent" as used herein refers to any element, molecule, functional group, compound, fragments thereof or moiety that facilitates detection of an agent (e.g., a polysaccharide nanoparticle) to which it is joined. Examples of imaging agents include, but are not limited to: various ligands, radionuclides (e.g., $^{3}$H, $^{14}$C, $^{18}$F, $^{19}$F, $^{32}$P, $^{35}$S, $^{135}$I, $^{125}$I, $^{123}$I, $^{64}$Cu, $^{187}$Re, $^{111}$In, $^{90}$Y, $^{90m}$Tc, $^{177}$Lu, $^{89}$Zr etc.), fluorescent dyes (for specific exemplary fluorescent dyes, see below), chemiluminescent agents (such as, for example, acridinum esters, stabilized dioxetanes, and the like), bioluminescent agents, spectrally resolvable inorganic fluorescent semiconductors nanocrystals (i.e., quantum dots), metal nanoparticles (e.g., gold, silver, copper, platinum, etc.) nanoclusters, paramagnetic metal ions, enzymes (for specific examples of enzymes, see below), colorimetric labels (such as, for example, dyes, colloidal gold, and the like), biotin, dioxigenin, haptens, and proteins for which antisera or monoclonal antibodies are available.

"Image": The term "image", as used herein, is understood to mean a visual display or any data representation that may be interpreted for visual display. For example, a three-dimensional image may include a dataset of values of a given quantity that varies in three spatial dimensions. A three-dimensional image (e.g., a three-dimensional data representation) may be displayed in two-dimensions (e.g., on a two-dimensional screen, or on a two-dimensional printout). In certain embodiments, the term "image" may refer to, for example, to a multi-dimensional image (e.g., a multi-dimensional (e.g., four dimensional) data representation) that is displayed in two-dimensions (e.g., on a two-dimensional screen, or on a two-dimensional printout). The term "image" may refer, for example, to an optical image, an x-ray image, an image generated by: positron emission tomography (PET), magnetic resonance, (MR) single photon emission computed tomography (SPECT), and/or ultrasound, and any combination of these.

"Nanoparticle": As used herein, the term "nanoparticle" refers to a particle having a diameter of less than 1000 nanometers (nm). In some embodiments, a nanoparticle has a diameter of less than 300 nm, as defined by the National Science Foundation. In some embodiments, a nanoparticle has a diameter of less than 100 nm as defined by the National Institutes of Health. In some embodiments, nanoparticles are micelles in that they comprise an enclosed compartment, separated from the bulk solution by a micellar membrane, typically comprised of amphiphilic entities which surround and enclose a space or compartment (e.g., to define a lumen). In some embodiments, a micellar membrane is comprised of at least one polymer, such as for example a biocompatible and/or biodegradable polymer.

"Peptide" or "Polypeptide": The term "peptide" or "polypeptide" refers to a string of at least two (e.g., at least three) amino acids linked together by peptide bonds. In certain embodiments, a polypeptide comprises naturally-occurring amino acids; alternatively or additionally, in certain embodiments, a polypeptide comprises one or more non-natural amino acids (i.e., compounds that do not occur in nature but that can be incorporated into a polypeptide chain; see, for example, http://www.cco.caltech.edu/~dadgrp/Unnatstruct-.gif, which displays structures of non-natural amino acids that have been successfully incorporated into functional ion channels) and/or amino acid analogs as are known in the art may alternatively be employed). In certain embodiments, one or more of the amino acids in a protein may be modified, for example, by the addition of a chemical entity such as a carbohydrate group, a phosphate group, a farnesyl group, an isofarnesyl group, a fatty acid group, a linker for conjugation, functionalization, or other modification, etc.

"Protein": As used herein, the term "protein" refers to a polypeptide (i.e., a string of at least 3-5 amino acids linked to one another by peptide bonds). Proteins may include moieties other than amino acids (e.g., may be glycoproteins, proteoglycans, etc.) and/or may be otherwise processed or modified. In certain embodiments "protein" can be a complete polypeptide as produced by and/or active in a cell (with or without a signal sequence); in certain embodiments, a "protein" is or comprises a characteristic portion such as a polypeptide as produced by and/or active in a cell. In certain embodiments, a protein includes more than one polypeptide chain. For example, polypeptide chains may be linked by one or more disulfide bonds or associated by other means. In certain embodiments, proteins or polypeptides as described herein may contain L-amino acids, D-amino acids, or both, and/or may contain any of a variety of amino acid modifications or analogs known in the art. Useful modifications include, e.g., terminal acetylation, amidation, methylation, etc. In certain embodiments, proteins or polypeptides may comprise natural amino acids, non-natural amino acids, synthetic amino acids, and/or combinations thereof. In certain embodiments, proteins are or comprise antibodies, antibody polypeptides, antibody fragments, biologically active portions thereof, and/or characteristic portions thereof.

"Pharmaceutical composition": As used herein, the term "pharmaceutical composition" refers to an active agent, formulated together with one or more pharmaceutically acceptable carriers. In certain embodiments, active agent is present in unit dose amount appropriate for administration in a therapeutic regimen that shows a statistically significant probability of achieving a predetermined therapeutic effect when administered to a relevant population. In certain embodiments, pharmaceutical compositions may be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream, or foam; sublingually; ocularly; transdermally; or nasally, pulmonary, and to other mucosal surfaces.

"Radiolabel": As used herein, "radiolabel" refers to a moiety comprising a radioactive isotope of at least one element. Exemplary suitable radiolabels include but are not limited to those described herein. In certain embodiments, a radiolabel is one used in positron emission tomography (PET). In certain embodiments, a radiolabel is one used in single-photon emission computed tomography (SPECT). In certain embodiments, radioisotopes comprise $^{99m}$Tc, $^{111}$In, $^{64}$Cu, $^{67}$Ga, $^{186}$Re, $^{188}$Re, $^{153}$Dm, $^{177}$Lu, $^{67}$Cu, $^{123}$I, $^{124}$I, $^{125}$I, $^{11}$C, $^{13}$N, $^{15}$O, $^{18}$F, $^{186}$Re, $^{188}$Re, $^{153}$Sm, $^{166}$Ho, $^{177}$Lu, $^{149}$Pm, $^{90}$Y, $^{213}$Bi, $^{103}$Pd, $^{109}$Pd, $^{159}$Gd, $^{140}$La, $^{198}$Au, $^{199}$Au, $^{169}$Yb, $^{175}$Yb, $^{165}$Dy, $^{166}$Dy, $^{67}$Cu, $^{105}$Rh, $^{111}$Ag, $^{89}$Zr, $^{225}$Ac, and $^{192}$Ir.

"Sensor": As used herein, the term "sensor" includes any sensor of electromagnetic radiation including, but not limited to, CCD camera, photomultiplier tubes, photodiodes, and avalanche photodiodes, unless otherwise evident from the context.

"Subject": As used herein, the term "subject" includes humans and mammals (e.g., mice, rats, pigs, cats, dogs, and horses). In many embodiments, subjects are mammals, particularly primates, especially humans. In certain embodiments, subjects are livestock such as cattle, sheep, goats, cows, swine, and the like; poultry such as chickens, ducks, geese, turkeys, and the like; and domesticated animals particularly pets such as dogs and cats. In certain embodiments (e.g., particularly in research contexts) subject mammals will be, for example, rodents (e.g., mice, rats, hamsters), rabbits, primates, or swine such as inbred pigs and the like.

"Substantially": As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

"Therapeutic agent": As used herein, the phrase "therapeutic agent" refers to any agent that has a therapeutic effect and/or elicits a desired biological and/or pharmacological effect, when administered to a subject.

"Therapeutically effective amount": as used herein, "therapeutically effective amount" refers to an amount that produces the desired effect for which it is administered. In certain embodiments, the term refers to an amount that is sufficient, when administered to a population suffering from or susceptible to a disease, disorder, and/or condition in accordance with a therapeutic dosing regimen, to treat the disease, disorder, and/or condition. In certain embodiments, a therapeutically effective amount is one that reduces the incidence and/or severity of, and/or delays onset of, one or more symptoms of the disease, disorder, and/or condition. Those of ordinary skill in the art will appreciate that the term "therapeutically effective amount" does not in fact require successful treatment be achieved in a particular individual. Rather, a therapeutically effective amount may be that amount that provides a particular desired pharmacological response in a significant number of subjects when adminis- tered to patients in need of such treatment. In certain embodiments, reference to a therapeutically effective amount may be a reference to an amount as measured in one or more specific tissues (e.g., a tissue affected by the disease, disorder or condition) or fluids (e.g., blood, saliva, serum, sweat, tears, urine, etc.). Those of ordinary skill in the art will appreciate that, in certain embodiments, a therapeuti- cally effective amount of a particular agent or therapy may be formulated and/or administered in a single dose. In certain embodiments, a therapeutically effective agent may be formulated and/or administered in a plurality of doses, for example, as part of a dosing regimen.

"Treatment": As used herein, the term "treatment" (also "treat" or "treating") refers to any administration of a substance that partially or completely alleviates, amelio- rates, relives, inhibits, delays onset of, reduces severity of, and/or reduces incidence of one or more symptoms, features, and/or causes of a particular disease, disorder, and/or con- dition. Such treatment may be of a subject who does not exhibit signs of the relevant disease, disorder and/or condi- tion and/or of a subject who exhibits only early signs of the disease, disorder, and/or condition. Alternatively or addi- tionally, such treatment may be of a subject who exhibits one or more established signs of the relevant disease, disorder and/or condition. In certain embodiments, treatment may be of a subject who has been diagnosed as suffering from the relevant disease, disorder, and/or condition. In certain embodiments, treatment may be of a subject known to have one or more susceptibility factors that are statistically cor- related with increased risk of development of the relevant disease, disorder, and/or condition. In certain embodiments, treatment comprises delivery of therapeutics, including but not limited to, small molecule delivery, radiotherapy, immu- notherapy, intrinsic therapeutic properties (e.g., ferroptosis), and particle-driven regulation of the tumor microenviron- ment. In certain embodiments, therapeutics are attached to particles, such as those described herein.

Drawings are presented herein for illustration purposes, not for limitation.

BRIEF DESCRIPTION OF DRAWINGS

The foregoing and other objects, aspects, features, and advantages of the present disclosure will become more apparent and better understood by referring to the following description taken in conduction with the accompanying drawings, in which:

14

Figure 1:
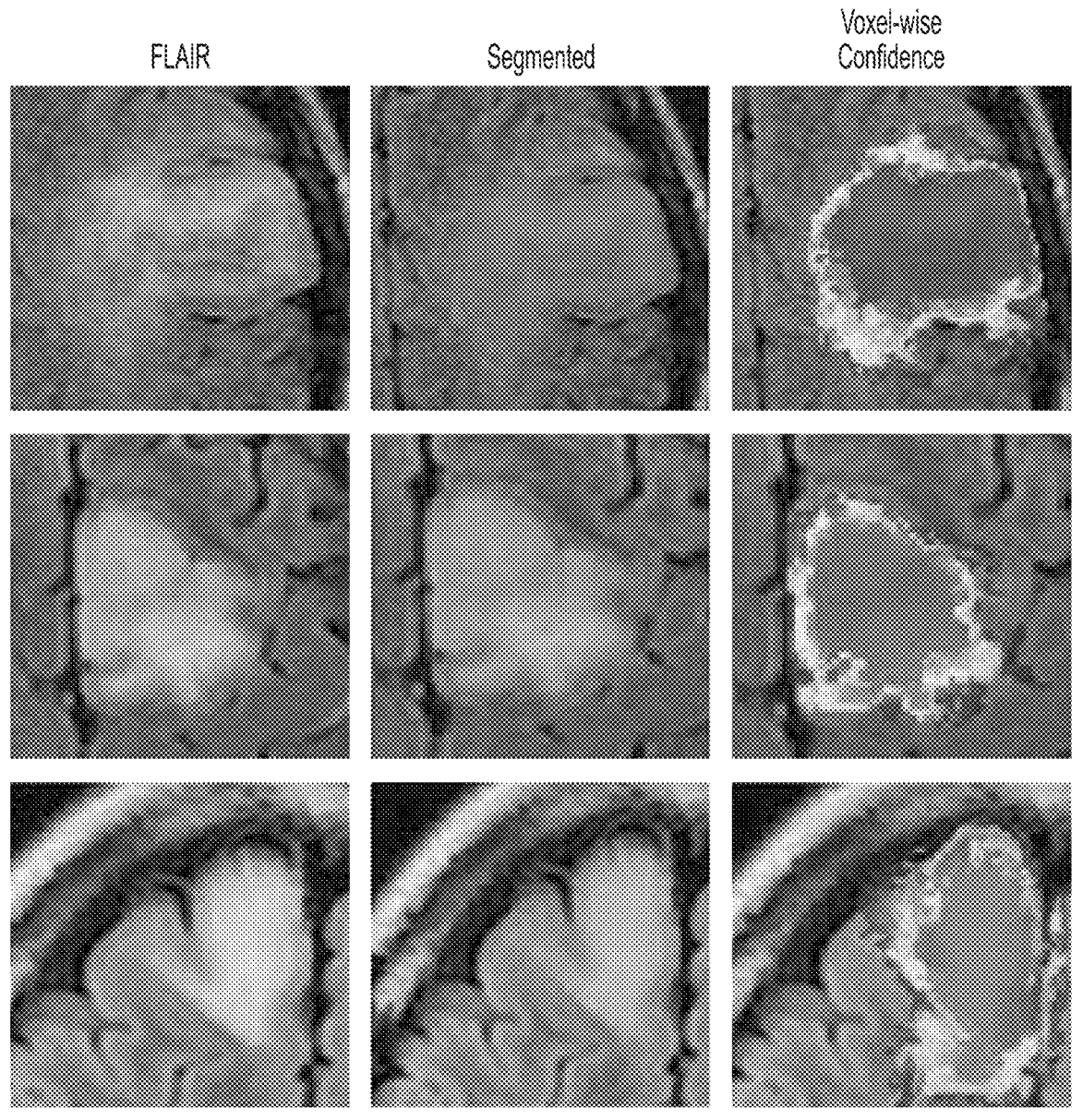

FIG. 1 shows that a semi-automated confidence-based segmentation results in three different gliomas with corre- sponding confidence scores (red=higher, and blue=lower confidence). Experiments in 30 gliomas resulted in a seg- mentation accuracy of 0.8±0.1 (1=best segmentation).

Figure 2:
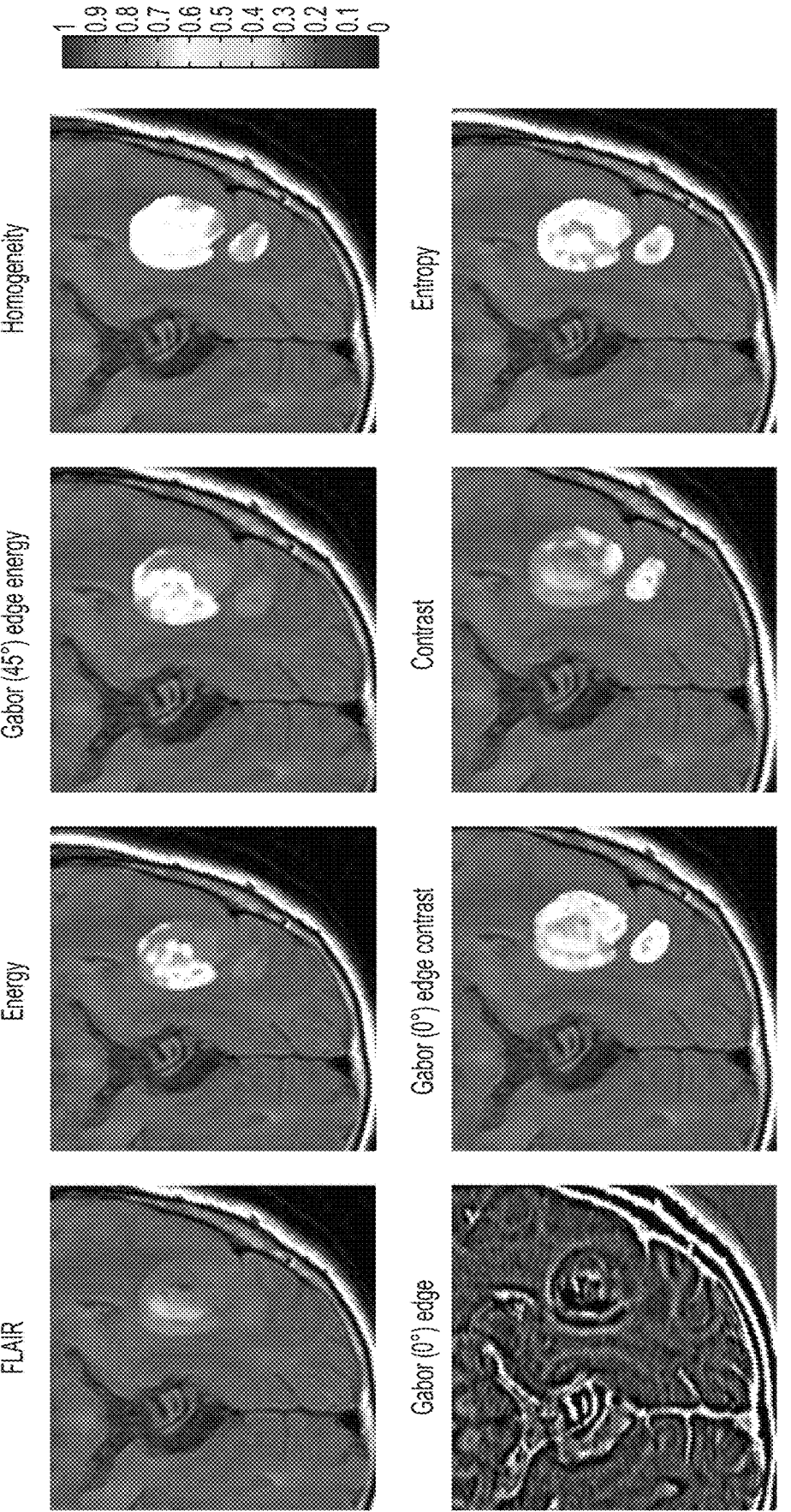

FIG. 2 shows exemplary images including textures, Gabor edges (at 4 different orientations), and textures on Gabor features that were computed on local patches to generate texture images in a glioma. Mean, kurtosis, and skewness summarized features such as Haralick textures (energy, entropy, correlation, homogeneity, contrast) and Haralick textures on Gabor edges (0°, 45°, 90°, 135°).

Figure 3:
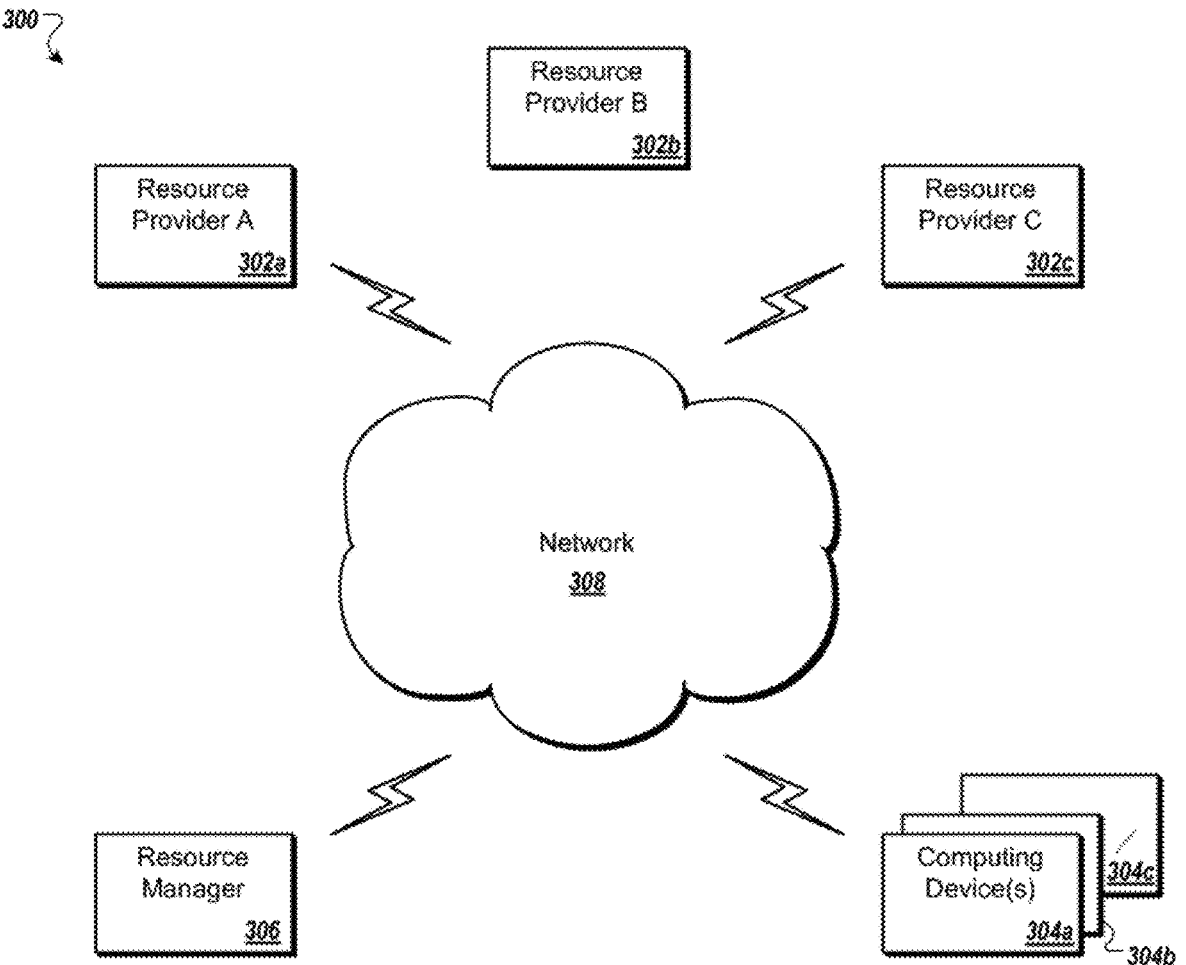

FIG. 3 is a block diagram of an example network envi- ronment for use in the methods and systems for analysis of spectrometry data, according to an illustrative embodiment.

Figure 4:
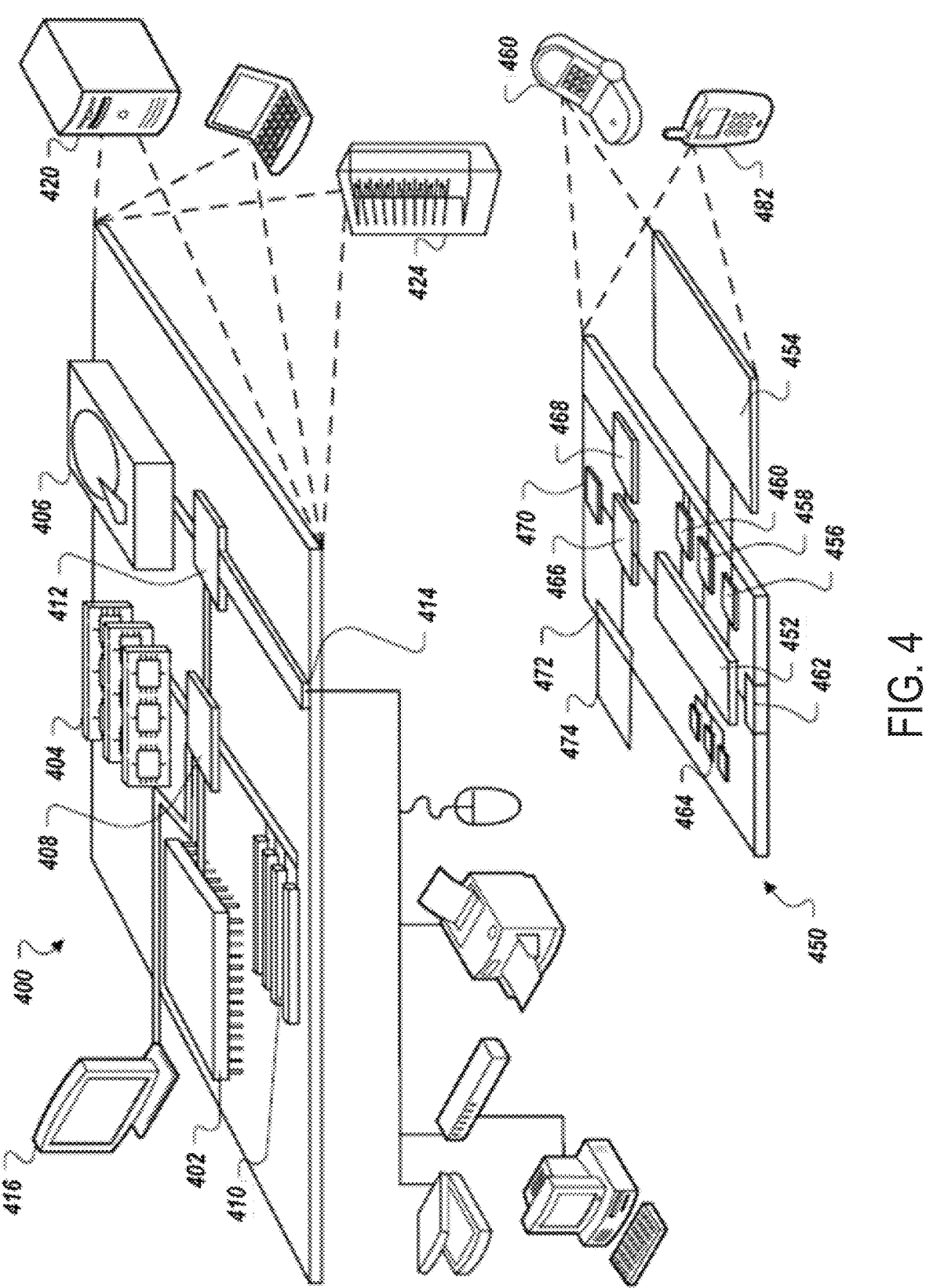

FIG. 4 is a block diagram of an example computing device and an example mobile computing device, for use in illustrative embodiments of the invention.

Figure 5:
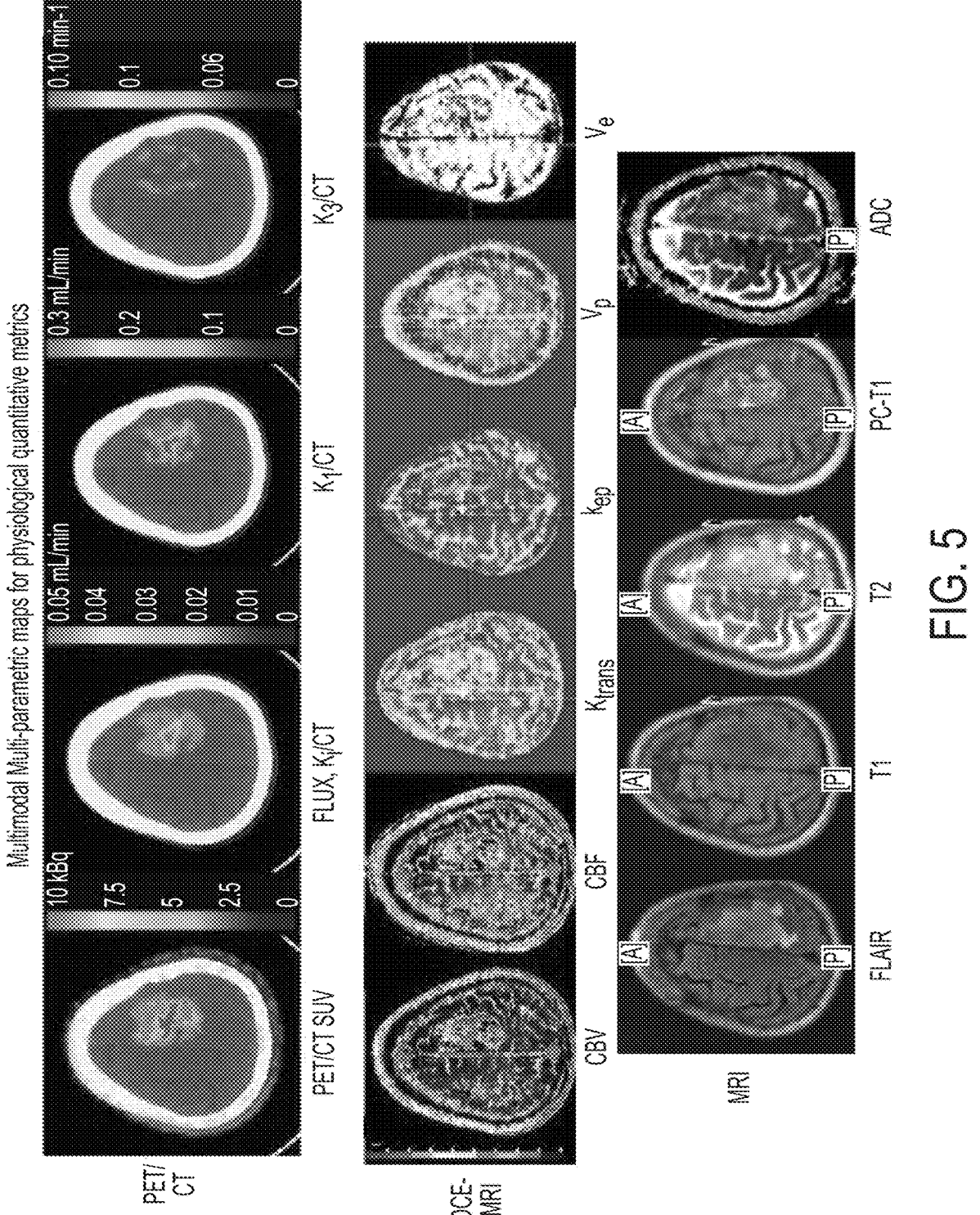

FIG. 5 shows multimodal multi-parametric maps (e.g., PET/CT, DCE-MRI, MRI) for physiological quantitative metrics.

Figure 6A:
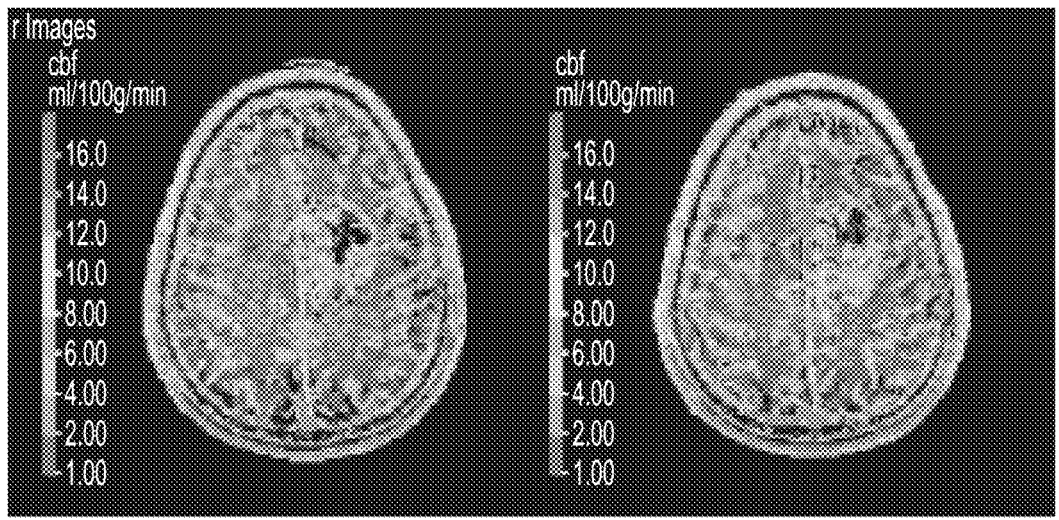

FIG. 6A shows cerebral blood flow (CBF) maps P1.

Figure 6B:
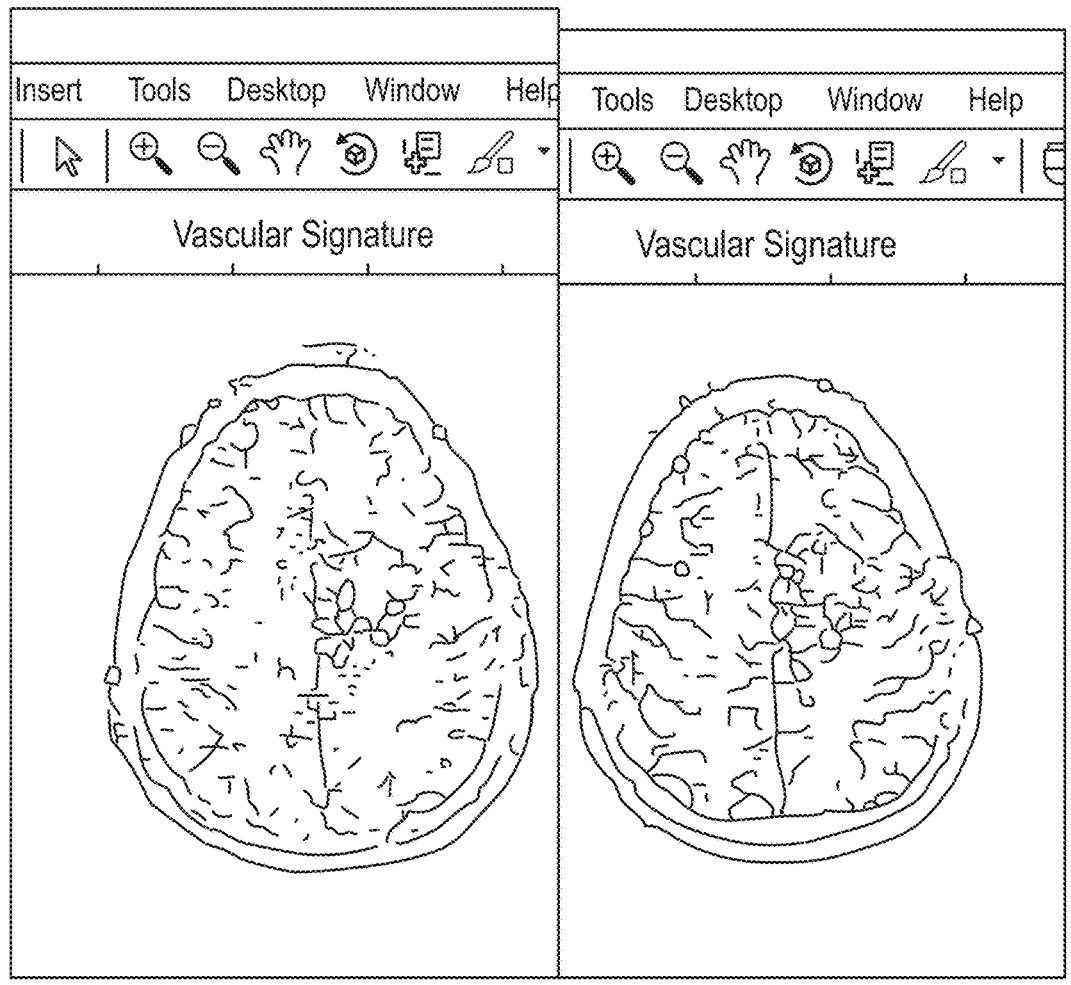

FIG. 6B shows vascular signatures corresponding to CBF maps P1.

Figure 7A:
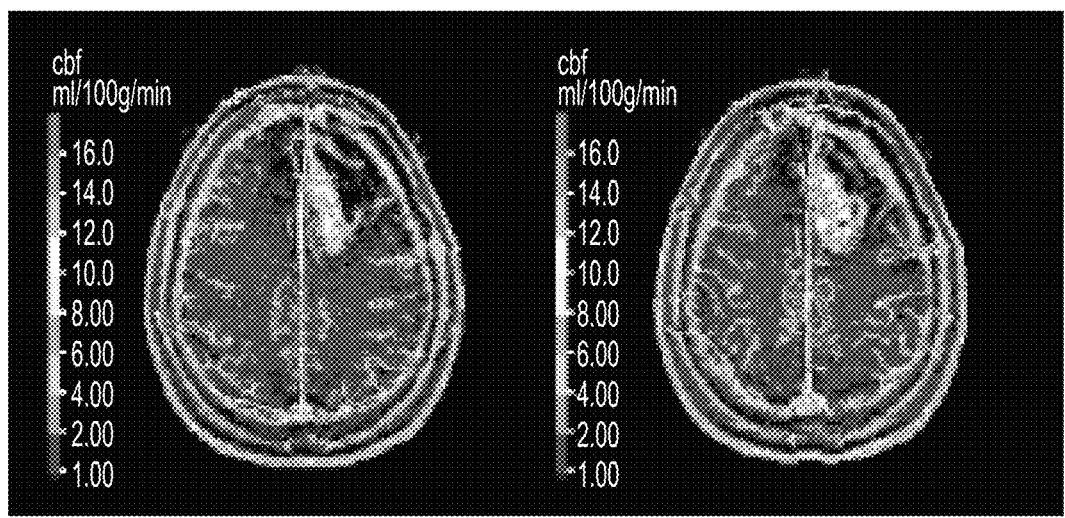

FIG. 7A shows cerebral blood flow maps P2.

Figure 7B:
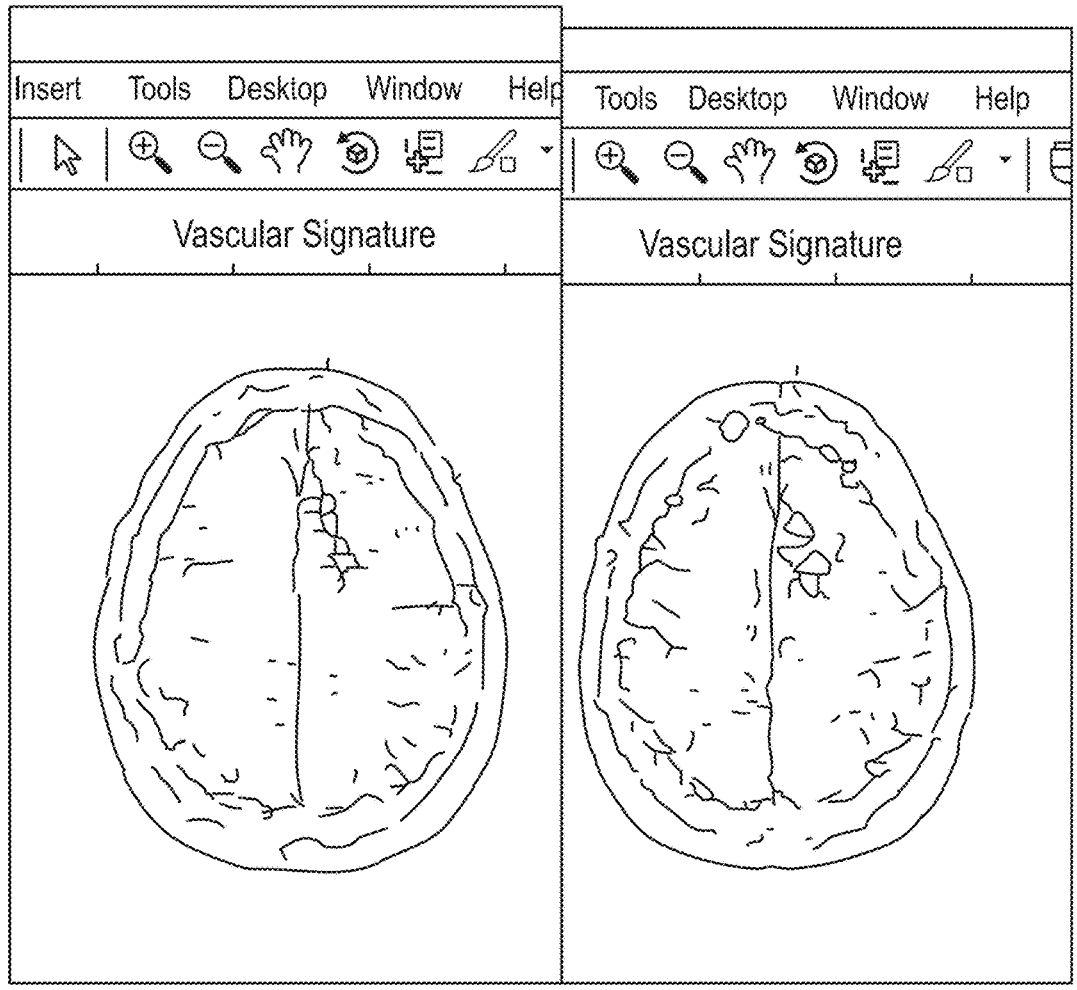

FIG. 7B shows vascular signatures corresponding to CBF maps P2.

Figure 8:
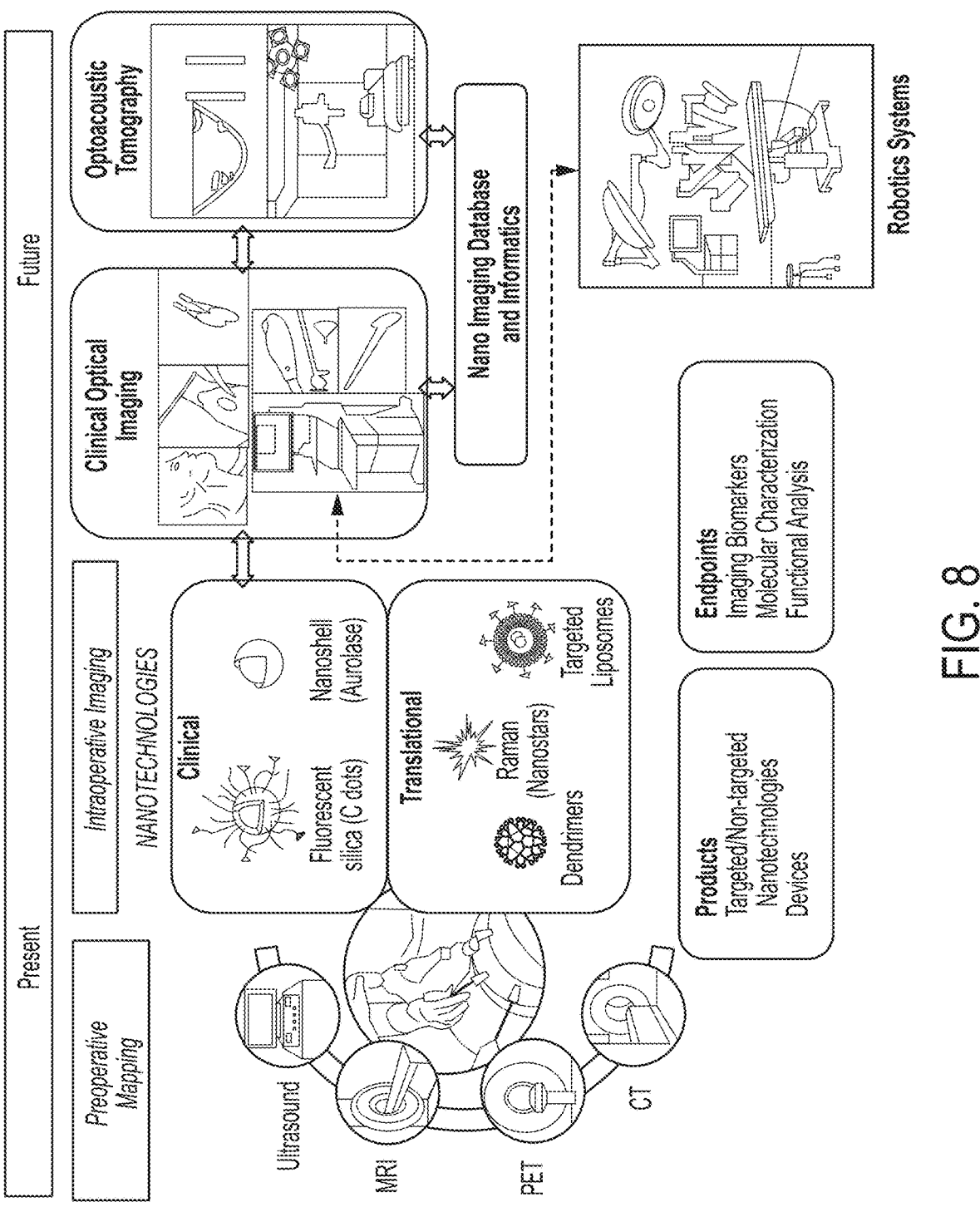

FIG. 8 shows a paradigm shift from preoperative and intraoperative imaging techniques using nanotechnologies to clinical optical imaging, optoacoustic tomography using nano imaging database and informatics and robotics sys- tems.

FIG. 9 is a flow chart depicting an in vivo method for determining intratumoral and/or interstitial nanoparticle dis- tribution in a tissue (e.g., a metastatic disease that goes to the brain, e.g., a primary glioma, e.g., a low-grade glioma, e.g., high-grade glioma) of a subject, according to an illustrative embodiment of the invention.

Figure 10:
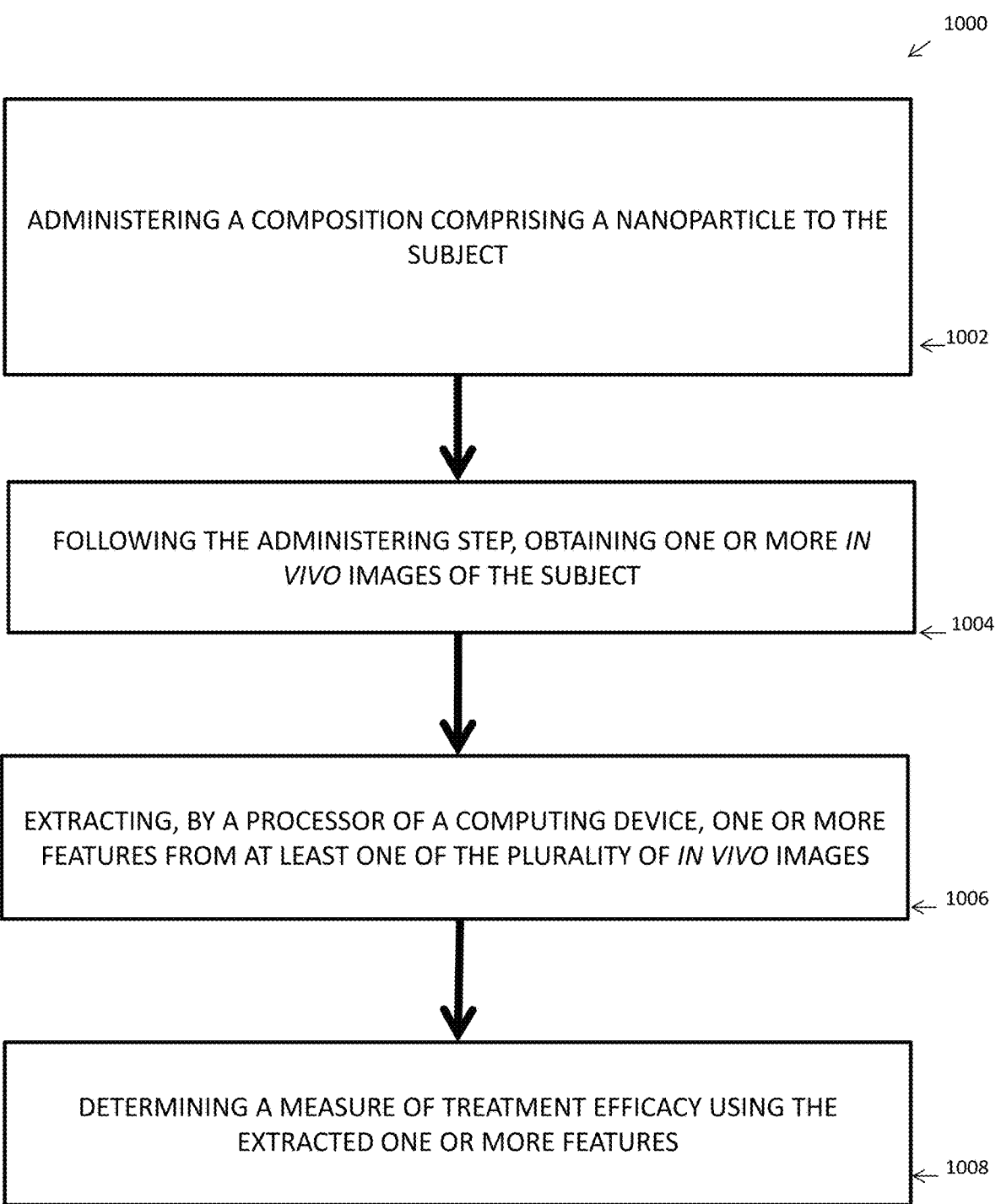

FIG. 10 is a flow chart depicting a method for identifying texture features (e.g., quantitative functional MR texture features) to predict treatment efficacy in a tissue (e.g., a metastatic disease that goes to the brain, e.g., a primary glioma, e.g., high-grade glioma, e.g., low-grade glioma) of a subject, according to an illustrative embodiment of the invention.

Figure 11:
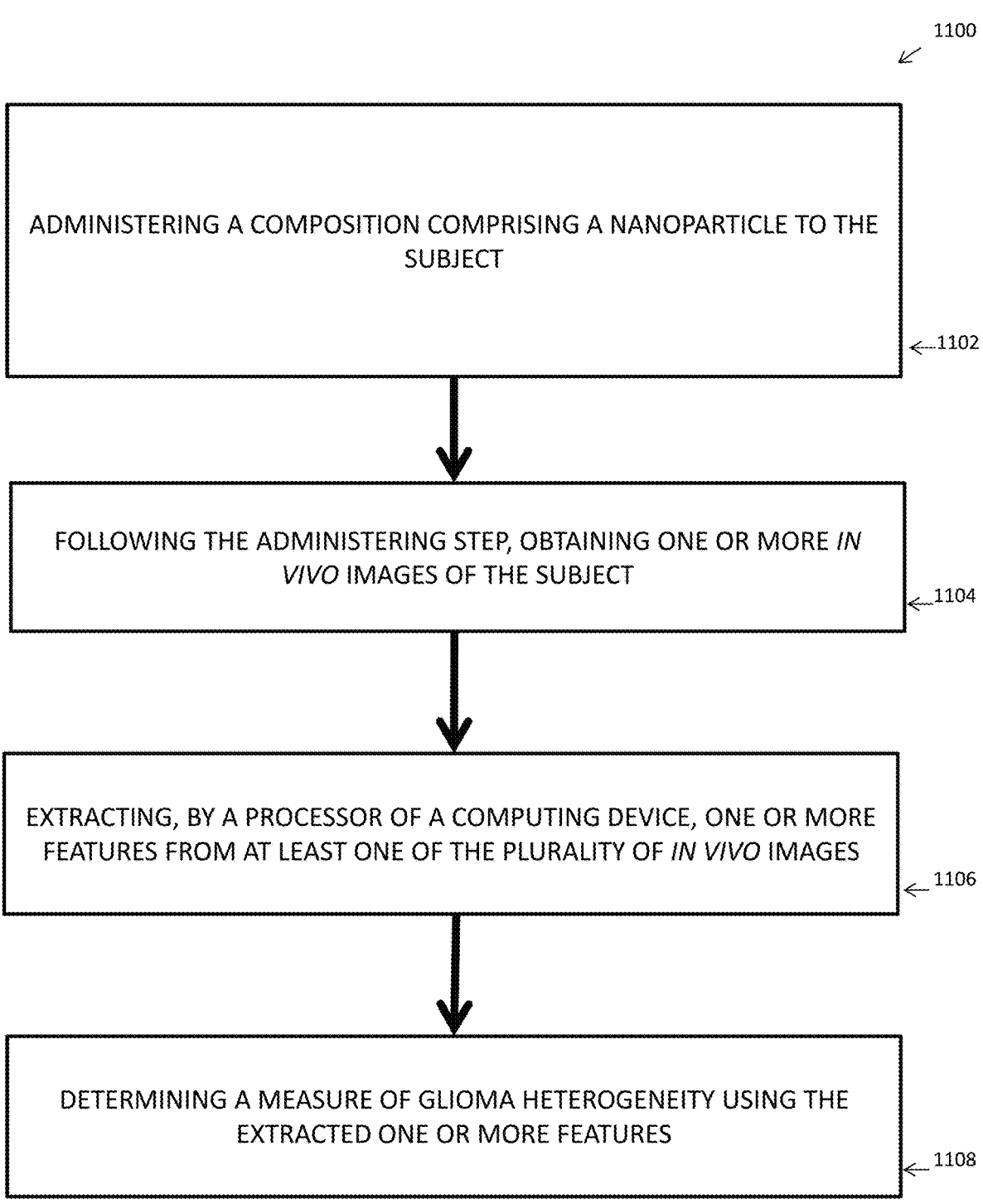

FIG. 11 is a flow chart depicting a method for evaluating glioma heterogeneity, according to an illustrative embodi- ment of the invention.

Figure 12:
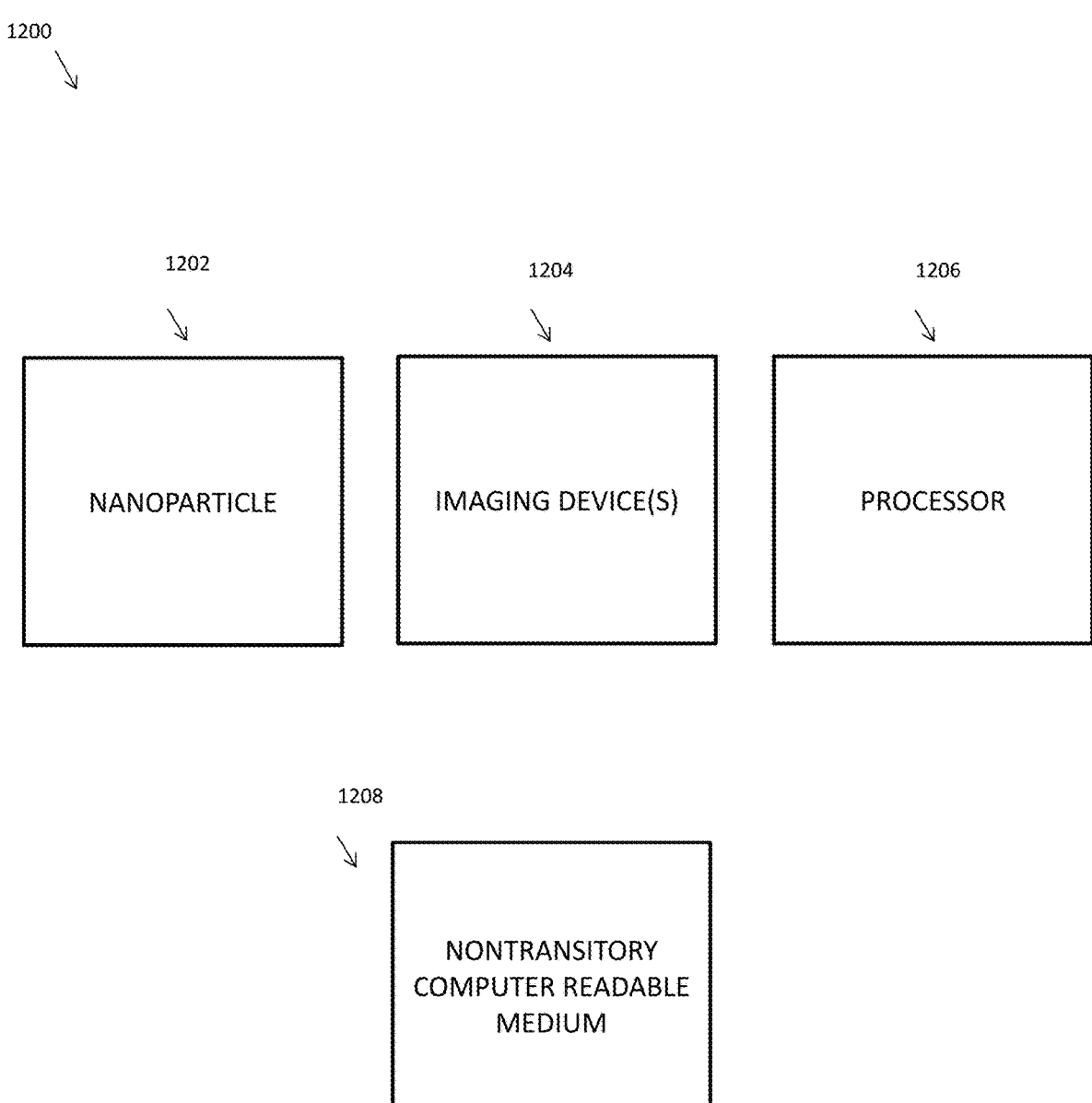

FIG. 12 is a schematic of a system comprising a nanopar- ticle, one or more imaging device(s), and a processor, according to an illustrative embodiment of the invention.

DETAILED DESCRIPTION

Throughout the description, where compositions are described as having, including, or comprising specific com- ponents, or where methods are described as having, includ- ing, or comprising specific steps, it is contemplated that, additionally, there are compositions of the present invention that consist essentially of, or consist of, the recited compo- nents, and that there are methods according to the present invention that consist essentially of, or consist of, the recited processing steps.

It should be understood that the order of steps or order for performing certain action is immaterial so long as the invention remains operable. Moreover, two or more steps or actions may be conducted simultaneously.

The mention herein of any publication, for example, in the Background section, is not an admission that the publication serves as prior art with respect to any of the claims presented herein. The Background section is presented for purposes of clarity and is not meant as a description of prior art with respect to any claim.

Described herein are particle-driven radiogenomics systems and methods that can be used to identify imaging features for prediction of intratumoral and interstitial nanoparticle distributions in cancers (e.g., in a metastatic disease that goes to the brain, e.g., low-grade and/or high-grade brain cancers (e.g., gliomas)). In certain embodiments, the systems and methods described herein extract and combine quantitative multi-dimensional data generated from structural, functional, and/or metabolic imaging. In certain embodiments, the combined multidimensional data is linked to intratumoral and interstitial nanoparticle distributions. For example, this linked data can be used to determine quantitative functional-metabolic multimodality particle-based imaging features and to predict treatment efficacy.

Systems and methods described herein include the following techniques: (1) particle-driven (versus molecularly-driven) radiomics; (2) fusion of structural with functional (and metabolic) imaging data sets; (3) structural imaging techniques beyond texture analysis, and (4) extraction of robust imaging features derived from molecular therapeutic experiments to determine treatment efficacy (e.g., as inhibitors are attached to particle probes). These techniques provide an improved quantitative ability to measure treatment response and determine tumor progressions compared to traditional size-based imaging methods.

Radiogenomics can be used to identify imaging biomarkers that identify the genomics of a disease, e.g., without the use of a biopsy. For example, statistically significant correlations can be determined between the genomics of a disease and MRI, CT, PET, and/or SPECT imaging features. Exemplary quantitative imaging features that can be extracted through radiomics include textural features, functional parameters, and clusters of features from multiparametric imaging. Radiogenomic analyses define relationships—or association maps—between such imaging features and molecular markers (omics), thus establishing a connection between diagnostic imaging (e.g., sentinel lymph node mapping, surgical margin mapping, reverse nodal mapping, functional intraoperative imaging) and molecular diagnostics.

Particle-driven radiogenomics identifies key prognostic imaging features, better understands tumor heterogeneity and treatment response, and guides molecularly-driven biopsies. Accordingly, particle-driven radiogenomics provides complementary and interchangeable information relative to other sources (e.g., demographics, pathology, blood biomarkers, or genomics) and improves individualized treatment selection and monitoring. The systems and methods described herein can have large clinical impact, since imaging is routinely used in clinical practice worldwide at low cost.

Embodiments can be used, for example, to help a physician, surgeon, or other medical personnel or researcher to identify and characterize areas of disease. Radiomics converts imaging data into a high dimensional mineable feature space using a large number of automatically extracted data-characterization algorithms. These imaging features capture distinct phenotypic differences of tumors and may have prognostic power and thus clinical significance across different diseases. Radiomics enables the high-throughput extraction and analysis of large amounts (e.g., over 400) of advanced quantitative imaging features (e.g., structural, functional, metabolic) with high throughput from clinical images obtained using CT, PET, or MRI, providing a comprehensive quantification of the tumor phenotype. Notably, these data can be extracted from standard-of-care images, leading to a very large potential subject pool.

Radiomics data are in a mineable form that can be used to build descriptive and predictive models relating image features to phenotypes or gene-protein signatures. The core hypothesis of radiomics is that these models, which can include biological or medical data, can provide valuable diagnostic, prognostic or predictive information.

Radiomics can be divided into distinct processes, for example: (a) image acquisition and reconstruction, (b) image segmentation and rendering, (c) feature extraction and feature qualification, and (d) databases and data sharing for eventual (e) ad hoc informatics analyses. Features can be generated that robustly reflect the complexity of the individual volumes. Informatics databases can incorporate image features, image annotations, and medical and genetic data. Statistical approaches can be optimally applied for data analysis.

The use of in vivo quantitative prognostic and predictive imaging biomarkers, such as those provided by radiomics analyses, can help select the right patient for the right treatment at the right time.

Particle-driven radiogenomics can lead to more uniform intratumoral distributions, in addition to improving targeted delivery to cancer cells. Such an analysis is critical to establishing whether or not a specific platform technology can serve as an effective vehicle for delivering small molecular drugs and other agents to tumors, which is thought to occur primarily via convection across the blood-tumor barrier, followed by intratumoral diffusion. In certain embodiments, the methods can be used in the detection, characterization and/or determination of the localization of a disease, especially early disease, the severity of a disease or a disease-associated condition, the staging of a disease, and monitoring and guiding various therapeutic interventions, such as surgical procedures, and monitoring and/or development of drug therapy and delivery, including cell based therapies.

Specific imaging features, in addition to genetic mutations and disease history, can be used to better stratify patients to appropriate treatment arms that may incorporate nanoparticle drug conjugates (NDCs) as part of a combinatorial strategy. Detail on NDCs is described, for example, in U.S. Publication No. 2015/0343091 A1 by Bradbury et al., the contents of which is hereby incorporated by reference herein in its entirety. NDCs, in certain embodiments, comprise a non-toxic, multi-modality, clinically proven silica-based nanoparticle platform with covalently attached drug molecules/moieties. The combination of size, molecular composition and chemistry (e.g., mode of drug release) may leverage the beneficial properties seen in other nanotherapeutic products with the aim of overcoming key obstacles hampering traditional formulations, including narrow therapeutic indices, dose-limiting toxicities, and limited clinical utility. NDCs also demonstrate imaging capabilities and targeting ligands which efficiently clear through the kidneys. Furthermore, the conjugates incorporate therapeutic agents for cancer detection, prevention, and/or treatment.

Given the heterogeneity of malignant brain tumors and multi-compartmental barriers to effective delivery, the use of such quantitative predictive imaging biomarkers, such as those provided by radiomics analyses, is essential to selecting the right patient at the right time for particle-based adjuvant therapies.

Details of various embodiments applicable to the systems and methods described herein are also provided in, for example, PCT/US14/30401 (WO 2014/145606) by Bradbury et al., PCT/US16/26434 ("Nanoparticle Immunoconjugates", filed Apr. 7, 2016) by Bradbury et al., PCT/US14/73053 (WO2015/103420) by Bradbury et al., PCT/US15/65816 (WO 2016/100340) by Bradbury et al., PCT/US16/34351 ("Methods and Treatment Using Ultrasmall Nanoparticles to Induce Cell Death of Nutrient-Deprived Cancer Cells via Ferroptosis", filed May 26, 2016) by Bradbury et al., U.S. 62/267,676 ("Compositions Comprising Cyclic Peptides, and Use of Same for Visual Differentiation of Nerve Tissue During Surgical Procedures" filed Dec. 15, 2015) by Bradbury et al., U.S. 62/330,029 ("Compositions and Methods for Targeted Particle Penetration, Distribution, and Response in Malignant Brain Tumors," filed Apr. 29, 2016) by Bradbury et al., and U.S. 62/349,538 ("Imaging Systems and Methods for Lymph Node Differentiation and/or Nerve Differentiation, e.g., for Intraoperative Visualization," filed Jun. 13, 2016) by Bradbury et al., the contents of which are hereby incorporated by reference in their entireties.

For example, in certain embodiments, an ultra-small (e.g., having a diameter less than 20 nm, e.g., having a diameter range from 5 nm to 10 nm), was tested in humans as is described in U.S. Publication No. 2014/0248210 A1, which is hereby incorporated by reference in its entirety. In this example, five patients had no adverse events and the agent was well tolerated over the study period. Pharmacokinetic behavior, expressed as the percentage of the injected dose per gram of tissue (% ID/g), versus time post-injection and the corresponding mean organ absorbed doses, were comparable to those found for other commonly used diagnostic radiotracers. Serial PET imaging of this representative patient showed progressive loss of presumed blood pool activity from major organs and tissues, with no appreciable activity seen by 72-hour post-injection (p.i.). Whole-body clearance half-times in these patients were estimated to range from 13-21 hours. Interestingly, there was no notable localization in the liver, spleen, or bone marrow, in contrast to many hydrophobic molecules, proteins, and larger particle platforms (greater than 10 nm). Although patients were pretreated with potassium iodide (KI) to block thyroid tissue uptake, a higher average absorbed thyroid dose was obtained in this patient relative to other tissues. Particles were also primarily excreted by the kidneys, with both kidney and bladder wall (after thyroid and tumor), demonstrating one of the highest % ID/g values by 72 hrs p.i.; as is often the case for renally excreted radiopharmaceuticals, the bladder wall received a higher average absorbed dose than other major organs and tissues. These findings highlight the fact that renal, rather than hepatobiliary, excretion is the predominant route of clearance from the body.

To date, no known particle-driven radiogenomics initiatives which identify key imaging features that may be used to predict intratumoral distributions in high-grade gliomas have been published. Such an assessment is particularly important for ultrasmall (e.g., sub 10-nm) particles, such as C′ dots, that are expected to exhibit improved diffusive properties within the tumor interstitium, relative to particles of larger size (e.g., greater than 20 nm in diameter).

In certain embodiments, the nanoparticle comprises silica, polymer (e.g., poly(lactic-co-glycolic acid) (PLGA)), biologics (e.g., protein carriers), and/or metal (e.g., gold, iron).

In certain embodiments, the nanoparticle is a "C dot" or "C′ dot" as described in U.S. Publication No. 2013/0039848 A1 by Bradbury et al. (see Appendix B), which is hereby incorporated by reference herein in its entirety.

In certain embodiments, the nanoparticle is spherical. In certain embodiments, the nanoparticle is non-spherical. In certain embodiments, the nanoparticle is or comprises a material selected from the group consisting of metal/semi-metal/non-metals, metal/semi-metal/non-metal-oxides, -sulfides, -carbides, -nitrides, liposomes, semiconductors, and/or combinations thereof. In certain embodiments, the metal is selected from the group consisting of gold, silver, copper, and/or combinations thereof.

The nanoparticle may comprise metal/semi-metal/non-metal oxides including silica ($SiO_2$), titania ($TiO_2$), alumina ($Al_2O_3$), zirconia ($Z_rO2$), germania ($GeO_2$), tantalum pentoxide ($Ta_2O_5$), $NbO_2$, etc., and/or non-oxides including metal/semi-metal/non-metal borides, carbides, sulfide and nitrides, such as titanium and its combinations (Ti, $TiB_2$, TiC, TiN, etc.).

In some embodiments, the silica-based nanoparticle platform comprises ultrasmall nanoparticles or "C dots," which are fluorescent, organo-silica core shell particles that have diameters controllable down to the sub-10 nm range with a range of modular functionalities. C dots are described by U.S. Pat. No. 8,298,677 B2 "Fluorescent silica-based nanoparticles", U.S. Publication No. 2013/0039848 A1 "Fluorescent silica-based nanoparticles", and U.S. Publication No. US 2014/0248210 A1 "Multimodal silica-based nanoparticles", the contents of which are incorporated herein by reference in their entireties. Incorporated into the silica matrix of the core are near-infrared dye molecules, such as Cy5.5, which provides its distinct optical properties. Surrounding the core is a layer or shell of silica. The silica surface is covalently modified with silyl-polyethylene glycol (PEG) groups to enhance stability in aqueous and biologically relevant conditions. These particles have been evaluated in vivo and exhibit excellent clearance properties owing largely to their size and inert surface. Among the additional functionalities incorporated into C dots are chemical sensing, non-optical (PET) image contrast and in vitro/in vivo targeting capabilities, which enable their use in visualizing lymph nodes for surgical applications, and melanoma detection in cancer.

C dots provide a unique platform for drug delivery due to their physical properties as well as demonstrated human in vivo characteristics. These particles are ultrasmall and benefit from EPR effects in tumor microenvironments, while retaining desired clearance and pharmacokinetic properties. To this end, in certain embodiments, drug constructs are covalently attached to C dots (or other nanoparticles). C dot-based nanoparticle systems for drug delivery provide good biostability, minimize premature drug release, and exhibit controlled release of the bioactive compound. In certain embodiments, peptide-based linkers are used for NDC and other applications described herein. These linkers, in the context of antibodies and polymers, are stable both in vitro and in vivo, with highly predictable release kinetics that rely on enzyme catalyzed hydrolysis by lysosomal proteases. For example, cathepsin B, a highly expressed protease in lysosomes, can be utilized to facilitate drug release from macromolecules. By incorporating a short, protease sensitive peptide between the macromolecular backbone and the drug molecule, controlled release of the drug can be obtained in the presence of the enzyme.

The nanoparticle may comprise one or more polymers, e.g., one or more polymers that have been approved for use in humans by the U.S. Food and Drug Administration (FDA) under 21 C.F.R. § 177.2600, including, but not limited to, polyesters (e.g., polylactic acid, poly(lactic-co-glycolic acid), polycaprolactone, polyvalerolactone, poly(1,3-dioxan-2-one)); polyanhydrides (e.g., poly(sebacic anhydride)); polyethers (e.g., polyethylene glycol); polyurethanes; polymethacrylates; polyacrylates; polycyanoacrylates; copolymers of PEG and poly(ethylene oxide) (PEO).

The nanoparticle may comprise one or more degradable polymers, for example, certain polyesters, polyanhydrides, polyorthoesters, polyphosphazenes, polyphosphoesters, certain polyhydroxyacids, polypropylfumerates, polycaprolactones, polyamides, poly(amino acids), polyacetals, polyethers, biodegradable polycyanoacrylates, biodegradable polyurethanes and polysaccharides. For example, specific biodegradable polymers that may be used include but are not limited to polylysine, poly(lactic acid) (PLA), poly (glycolic acid) (PGA), poly(caprolactone) (PCL), poly(lactide-co-glycolide) (PLG), poly(lactide-co-caprolactone) (PLC), and poly(glycolide-co-caprolactone) (PGC). Another exemplary degradable polymer is poly (beta-amino esters), which may be suitable for use in accordance with the present application.

The surface chemistry, uniformity of coating (where there is a coating), surface charge, composition, concentration, frequency of administration, shape, and/or size of the nanoparticle can be adjusted to produce a desired therapeutic effect.

In certain embodiments, a nanoparticle can have or be modified to have one or more functional groups. Such functional groups (within or on the surface of a nanoparticle) can be used for association with any agents (e.g., detectable entities, targeting entities, therapeutic entities, or PEG). In addition to changing the surface charge by introducing or modifying surface functionality, the introduction of different functional groups allows the conjugation of linkers (e.g., (cleavable or (bio-)degradable) polymers such as, but not limited to, polyethylene glycol, polypropylene glycol, PLGA, etc.), targeting/homing agents, and/or combinations thereof.

In certain embodiments, the nanoparticle comprises a therapeutic agent, e.g., a drug moiety (e.g., a chemotherapy drug) and/or a therapeutic radioisotope. As used herein, "therapeutic agent" refers to any agent that has a therapeutic effect and/or elicits a desired biological and/or pharmacological effect, when administered to a subject.

For example, the nanoparticles described herein demonstrate enhanced penetration of tumor tissue (e.g., brain tumor tissue) and diffusion within the tumor interstitium, e.g., for treatment of cancer (e.g., gliomas, e.g., high grade gliomas), as described in PCT/US17/30056 ("Compositions and Methods for Targeted Particle Penetration, Distribution, and Response in Malignant Brain Tumors," filed Apr. 28, 2016) by Bradbury et al., the contents of which is hereby incorporated by reference in its entirety. Further described are methods of targeting tumor-associated macrophages, microglia, and/or other cells in a tumor microenvironment using such nanoparticles.

Moreover, diagnostic, therapeutic, and theranostic (diagnostic and therapeutic) platforms featuring such nanoparticle conjugates are described for treating targets in both the tumor and surrounding microenvironment, thereby enhancing efficacy of cancer treatment. Use of the nanoparticles described herein with other conventional therapies, including chemotherapy, radiotherapy, immunotherapy, and the like, is also envisaged.

Multi-targeted kinase inhibitors and combinations of single-targeted kinase inhibitors have been developed to overcome therapeutic resistance. Importantly, multimodality combinations of targeted agents, including particle-based probes designed to carry small molecule inhibitors (SMIs), chemotherapeutics, radiotherapeutic labels, and/or immunotherapies can enhance treatment efficacy and/or improve treatment planning of malignant brain tumors. Coupled with molecular imaging labels, these vehicles permit monitoring of drug delivery, accumulation, and retention, which may, in turn, lead to optimal therapeutic indices.

Moreover, use of radiolabels and/or fluorescent markers attached to (or incorporated in or on, or otherwise associated with) the nanoparticles provide quantitative assessment of particle uptake and monitoring of treatment response. In various embodiments, modular linkers are described for incorporating targeting ligands to develop a drug delivery system with controlled pharmacological properties. The described platforms determine the influence of targeting on nanoparticle penetration and accumulation, thereby establishing an adaptable platform for improved delivery of a range of tractable SMIs, for example, to primary and metastatic brain tumors (e.g., gliomas (e.g., high grade gliomas, e.g., low grade gliomas).

In certain embodiments, the nanoparticle comprises one or more targeting ligands (or moieties) (e.g., attached thereto), such as, but not limited to, small molecules (e.g., folates, dyes, etc), aptamers (e.g., A10, AS1411), polysaccharides, small biomolecules (e.g., folic acid, galactose, bisphosphonate, biotin), oligonucleotides, and/or proteins (e.g., (poly)peptides (e.g., αMSH, RGD, octreotide, AP peptide, epidermal growth factor, chlorotoxin, transferrin, etc), antibodies, antibody fragments, proteins, etc.). In certain embodiments, the nanoparticle comprises one or more contrast/imaging agents (e.g., fluorescent dyes, (chelated) radioisotopes (SPECT, PET), MR-active agents, CT-agents), and/or therapeutic agents (e.g., small molecule drugs, therapeutic (poly)peptides, therapeutic antibodies, (chelated) radioisotopes, etc).

In certain embodiments, the nanoparticle comprises (e.g., has attached) one or more targeting ligands, e.g., for targeting cancer tissue/cells of interest.

The number of ligands attached to the nanoparticle may range from about 1 to about 20, from about 2 to about 15, from about 3 to about 10, from about 1 to about 10, or from about 1 to about 6. The small number of the ligands attached to the nanoparticle helps maintain the hydrodynamic diameter of the present nanoparticle which meet the renal clearance cutoff size range. Hilderbrand et al., Near-infrared fluorescence: application to in vivo molecular imaging, *Curr. Opin. Chem. Biol.,* 14:71-9, 2010.

In certain embodiments, a therapeutic agent may be attached to the nanoparticle. The therapeutic agents include antibiotics, antimicrobials, antiproliferatives, antineoplastics, antioxidants, endothelial cell growth factors, thrombin inhibitors, immunosuppressants, anti-platelet aggregation agents, collagen synthesis inhibitors, therapeutic antibodies, nitric oxide donors, antisense oligonucleotides, wound healing agents, therapeutic gene transfer constructs, extracellular matrix components, vasodilators, thrombolytics, anti-metabolites, growth factor agonists, antimitotics, statin, steroids, steroidal and non-steroidal anti-inflammatory agents, angiotensin converting enzyme (ACE) inhibitors, free radical scavengers, PPAR-gamma agonists, small interfering RNA (siRNA), microRNA, and anti-cancer chemotherapeutic agents. The therapeutic agents encompassed by the present embodiment also include radionuclides, for example, $^{90}$Y, $^{131}$I and $^{177}$Lu. The therapeutic agent may be radiolabeled, such as labeled by binding to radiofluorine $^{18}$F.

Example therapeutics and/or drugs that can be used include RTK inhibitors, such as dasatinib and gefitinib, can target either platelet-derived growth factor receptor (PDGFR) or EGFRmt+ expressed by primary tumor cells of human or murine origin (e.g., genetically engineered mouse models of high-grade glioma, neurospheres from human patient brain tumor explants) and/or tumor cell lines of non-neural origin. Dasatinib and gefitinib analogs can be synthesized to enable covalent attachment to several linkers without perturbing the underlying chemical structure defining the active binding site.

Cancers that may be treated include, for example, any cancer. In certain embodiments, the cancers are brain cancers, such as gliomas. In certain embodiments, the cancer is prostate cancer, melanoma, breast cancer, gynecological malignancies, or colorectal cancers.

In certain embodiments, a contrast agent may be attached to the present nanoparticle for medical or biological imaging. The imaging techniques encompassed In certain embodiments may include positron emission tomography (PET), single photon emission computed tomography (SPECT), computerized tomography (CT), magnetic resonance imaging (MRI), optical bioluminescence imaging, optical fluorescence imaging, and combinations thereof. In certain embodiments, the contrast agent can be any molecule, substance or compound known in the art for PET, SPECT, CT, MM, and optical imaging. The contrast agent may be radionuclides, radiometals, positron emitters, beta emitters, gamma emitters, alpha emitters, paramagnetic metal ions, and supraparamagnetic metal ions. The contrast agents include, but are not limited to, iodine, fluorine, Cu, Zr, Lu, At, Yt, Ga, In, Tc, Gd, Dy, Fe, Mn, Ba and BaSO$_4$. The radionuclides that may be used as the contrast agent attached to the nanoparticle of the present embodiment include, but are not limited to, $^{89}$Zr, $^{64}$Cu, $^{68}$Ga, $^{86}$Y, $^{124}$I and $^{177}$Lu. Alternatively, a contrast agent may be indirectly conjugated to the nanoparticle, by attaching to linkers or chelates. The chelate may be adapted to bind a radionuclide. The chelates that can be attached to the present nanoparticle may include, but are not limited to, 1,4,7,10-tetraazacyclododecane-1,4,7,10-tetraacetic acid (DOTA), diethylenetriaminepentaacetic (DTPA), desferrioxamine (DFO) and triethylenetetramine (TETA).

In certain embodiments, the nanoprobes comprises a chelator, for example, 1,4,8,11-tetraazabicyclo[6.6.2]hexadecane-4,11-diyl)diacetic acid (CB-TE2A); desferoxamine (DFO); diethylenetriaminepentaacetic acid (DTPA); 1,4,7,10-tetraazacyclotetradecane-1,4,7, 10-tetraacetic acid (DOTA); thylenediaminetetraacetic acid (EDTA); ethylene glycolbis(2-aminoethyl)-N,N,N',N'-tetraacetic acid (EGTA); 1,4,8,11-tetraazacyclotetradecane-1,4,8,11-tetraacetic acid (TETA); ethylenebis-(2-4 hydroxy-phenylglycine) (EHPG); 5-Cl-EHPG; 5Br-EHPG; 5-Me-EHPG; 5t-Bu-EHPG; 5-sec-Bu-EHPG; benzodiethylenetriamine pentaacetic acid (benzo-DTPA); dibenzo-DTPA; phenyl-DTPA, diphenyl-DTPA; benzyl-DTPA; dibenzyl DTPA; bis-2 (hydroxybenzyl)-ethylene-diaminediacetic acid (HBED) and derivatives thereof; Ac-DOTA; benzo-DOTA; dibenzo-DOTA; 1,4,7-triazacyclononane N,N',N''-triacetic acid (NOTA); benzo-NOTA; benzo-TETA, benzo-DOTMA, where DOTMA is 1,4,7,10-tetraazacyclotetradecane-1,4,7, 10-tetra(methyl tetraacetic acid), benzo-TETMA, where TETMA is 1,4,8,11-tetraazacyclotetradecane-1,4,8,11-(methyl tetraacetic acid); derivatives of 1,3-propylenediaminetetraacetic acid (PDTA); triethylenetetraaminehexaacetic acid (TTHA); derivatives of 1,5,10-N,N',N''-tris(2,3-dihydroxybenzoyl)-tricatecholate (LICAM); and 1,3,5-N,N',N''-tris(2,3-dihydroxybenzoyl)aminomethylbenzene (MECAM), or other metal chelators.

In certain embodiments, the nanoconjugate comprises more than one chelator.

In certain embodiments the radioisotope-chelator pair is $^{89}$Zr-DFO. In certain embodiments the radioisotope-chelator pair is $^{177}$Lu-DOTA. In certain embodiments, the radioisotope-chelator pair is $^{225}$Ac-DOTA.

In some embodiments, ultrasmall particles may be associated with PET labels and/or optical probes. Nanoparticles may be observed in vivo (e.g., via PET) to evaluate drug accumulation in a target site. For example, nanoparticles with PET labels (e.g., without drug substances) may be administered first. Then, by analyzing the in vivo PET images of the nanoparticles, drug (e.g., conjugated with nanoparticles) concentration and accumulation rate in the tumor may be estimated. The dose may be determined based on the obtained estimation to provide personalized medicine (e.g., tumor size rather than the patient's body weight). In some embodiments, a radiolabeled drug may be traced in vivo. A highly concentrated chemotherapy drug is potentially dangerous if it is not targeted. In some embodiments, nanoparticles with optical probes (e.g., fluorophore) may be used for intraoperative imaging (e.g., where surface of tissue/tumor is exposed) and/or biopsies of tumors.

In certain embodiments, a probe species comprises nanoparticles. In certain embodiments, the nanoparticles have a silica architecture and dye-rich core. In certain embodiments, the dye rich core comprises a fluorescent reporter. In certain embodiments, the fluorescent reporter is a near infrared or far red dye. In certain embodiments, the fluorescent reporter is selected from the group consisting of a fluorophore, fluorochrome, dye, pigment, fluorescent transition metal, and fluorescent protein. In certain embodiments, the fluorescent reporter is selected from the group consisting of Cy5, Cy5.5, Cy2, FITC, TRITC, Cy7, FAM, Cy3, Cy3.5, Texas Red, ROX, HEX, JA133, AlexaFluor 488, AlexaFluor 546, AlexaFluor 633, AlexaFluor 555, AlexaFluor 647, DAPI, TMR, R6G, GFP, enhanced GFP, CFP, ECFP, YFP, Citrine, Venus, YPet, CyPet, AMCA, Spectrum Green, Spectrum Orange, Spectrum Aqua, Lissamine and Europium. In certain embodiments, imaging is performed in normal lighting settings. In certain embodiments, imaging is performed with some to zero levels of ambient lighting settings.

The imaging methods herein can be used with a number of different fluorescent probe species (or, as in embodiments using a tandem bioluminescent reporter/fluorescent probe, the fluorescent species thereof), for example, (1) probes that become activated after target contact (e.g., binding or interaction) (Weissleder et al., *Nature Biotech.*, 17:375-378, 1999; Bremer et al., *Nature Med.*, 7:743-748, 2001; Campo et al., *Photochem. Photobiol.* 83:958-965, 2007); (2) wavelength shifting beacons (Tyagi et al., *Nat. Biotechnol.*, 18:1191-1196, 2000); (3) multicolor (e.g., fluorescent) probes (Tyagi et al., *Nat. Biotechnol.*, 16:49-53, 1998); (4) probes that have high binding affinity to targets, e.g., that remain within a target region while non-specific probes are cleared from the body (Achilefu et al., *Invest. Radiol.*, 35:479-485, 2000; Becker et al., *Nature Biotech.* 19:327-331, 2001; Bujai et al., *J. Biomed. Opt.* 6:122-133, 2001; Ballou et al. *Biotechnol. Prog.* 13:649-658, 1997; and Neri et al., *Nature Biotech* 15:1271-1275, 1997); (5) quantum dot or nanoparticle-based imaging probes, including multivalent imaging probes, and fluorescent quantum dots such as amine T2 MP EviTags® (Evident Technologies) or Qdot® Nanocrystals (Invitrogen™); (6) non-specific imaging probes e.g., indocyanine green, AngioSense® (VisEn Medical); (7) labeled cells (e.g., such as cells labeled using exogenous fluorophores such as VivoTag™ 680, nanoparticles, or quantum dots, or by genetically manipulating cells to express fluorescent or luminescent proteins such as green or red fluorescent protein; and/or (8) X-ray, MR, ultrasound, PET or SPECT contrast agents such as gadolinium, metal oxide nanoparticles, X-ray contrast agents including iodine based imaging agents, or radioisotopic form of metals such as copper, gallium, indium, technetium, yttrium, and lutetium including, without limitation, 99m-Tc, 111-In, 64-Cu, 67-Ga, 186-Re, 188-Re, 153-Sm, 177-Lu, and 67-Cu. The relevant text of the above-referenced documents are incorporated by reference herein. Another group of suitable imaging probes are lanthanide metal-ligand probes. Fluorescent lanthanide metals include europium and terbium. Fluorescence properties of lanthanides are described in Lackowicz, 1999, Principles of Fluorescence Spectroscopy, $2^{nd}$ Ed., Kluwar Academic, New York, the relevant text incorporated by reference herein. In the methods of this embodiment, the imaging probes can be administered systemically or locally by injecting an imaging probe or by topical or other local administration routes, such as "spraying". Furthermore, imaging probes used in the embodiment of this invention can be conjugated to molecules capable of eliciting photodynamic therapy. These include, but are not limited to, Photofrin, Lutrin, Antrin, aminolevulinic acid, hypericin, benzoporphyrin derivative, and select porphyrins. In certain embodiments, two or more probe species are graphically distinguished, e.g., are displayed with different colors (e.g., green and red, e.g., green and blue), to separately represent the two lymphatic drainage pathways and/or nodes. In certain embodiments, the representations of two or more probe species are superimposed on a graphical display, or the overlapping portion is represented with a different (e.g., a third) color (e.g., yellow). For example, for a lymphatic drainage pathway that both drains the extremity and leads to the tumor site, the pathway may contain both first and second probe species (corresponding, respectively, to a first and second color on the display), and the region of overlap on the display is assigned a new color different from the first and second color. The color may indicate that the associated node should not be removed, to avoid lymphedema.

In general, fluorescent quantum dots used in the practice of the elements of this invention are nanocrystals containing several atoms of a semiconductor material (including but not limited to those containing cadmium and selenium, sulfide, or tellurium; zinc sulfide, indium-antimony, lead selenide, gallium arsenide, and silica or ormosil), which have been coated with zinc sulfide to improve the properties of the fluorescent agents.

In particular, fluorescent probe species are a preferred type of imaging probe. A fluorescent probe species is a fluorescent probe that is targeted to a biomarker, molecular structure or biomolecule, such as a cell-surface receptor or antigen, an enzyme within a cell, or a specific nucleic acid, e.g., DNA, to which the probe hybridizes. Biomolecules that can be targeted by fluorescent imaging probes include, for example, antibodies, proteins, glycoproteins, cell receptors, neurotransmitters, integrins, growth factors, cytokines, lymphokines, lectins, selectins, toxins, carbohydrates, internalizing receptors, enzyme, proteases, viruses, microorganisms, and bacteria.

In certain embodiments, probe species have excitation and emission wavelengths in the red and near infrared spectrum, e.g., in the range 550-1300 or 400-1300 nm or from about 440 to about 1100 nm, from about 550 to about 800 nm, or from about 600 to about 900 nm. Use of this portion of the electromagnetic spectrum maximizes tissue penetration and minimizes absorption by physiologically abundant absorbers such as hemoglobin (<650 nm) and water (>1200 nm). Probe species with excitation and emission wavelengths in other spectrums, such as the visible and ultraviolet light spectrum, can also be employed in the methods of the embodiments of the present invention. In particular, fluorophores such as certain carbocyanine or polymethine fluorescent fluorochromes or dyes can be used to construct optical imaging agents, e.g. U.S. Pat. No. 6,747,159 to Caputo et al. (2004); U.S. Pat. No. 6,448,008 to Caputo et al. (2002); U.S. Pat. No. 6,136,612 to Della Ciana et al. (2000); U.S. Pat. No. 4,981,977 to Southwick, et al. (1991); U.S. Pat. No. 5,268,486 to Waggoner et al. (1993); U.S. Pat. No. 5,569,587 to Waggoner (1996); U.S. Pat. No. 5,569,766 to Waggoner et al. (1996); U.S. Pat. No. 5,486,616 to Waggoner et al. (1996); U.S. Pat. No. 5,627, 027 to Waggoner (1997); U.S. Pat. No. 5,808,044 to Brush, et al. (1998); U.S. Pat. No. 5,877,310 to Reddington, et al. (1999); U.S. Pat. No. 6,002,003 to Shen, et al. (1999); U.S. Pat. No. 6,004,536 to Leung et al. (1999); U.S. Pat. No. 6,008,373 to Waggoner, et al. (1999); U.S. Pat. No. 6,043, 025 to Minden, et al. (2000); U.S. Pat. No. 6,127,134 to Minden, et al. (2000); U.S. Pat. No. 6,130,094 to Waggoner, et al. (2000); U.S. Pat. No. 6,133,445 to Waggoner, et al. (2000); U.S. Pat. No. 7,445,767 to Licha, et al. (2008); U.S. Pat. No. 6,534,041 to Licha et al. (2003); U.S. Pat. No. 7,547,721 to Miwa et al. (2009); U.S. Pat. No. 7,488,468 to Miwa et al. (2009); U.S. Pat. No. 7,473,415 to Kawakami et al. (2003); also WO 96/17628, EP 0 796 111 B1, EP 1 181 940 B1, EP 0 988 060 B1, WO 98/47538, WO 00/16810, EP 1 113 822 B1, WO 01/43781, EP 1 237 583 A1, WO 03/074091, EP 1 480 683 B1, WO 06/072580, EP 1 833 513 A1, EP 1 679 082 A1, WO 97/40104, WO 99/51702, WO 01/21624, and EP 1 065 250 A1; and Tetrahedron Letters 41, 9185-88 (2000).

Exemplary fluorochromes for probe species include, for example, the following: Cy5.5, Cy5, Cy7.5 and Cy7 (GE® Healthcare); AlexaFluor660, AlexaFluor680, AlexaFluor790, and AlexaFluor750 (Invitrogen); VivoTag™680, VivoTag™-S680, VivoTag™-S750 (VisEn Medical); Dy677, Dy682, Dy752 and Dy780 (Dyomics®); DyLight® 547, and/or DyLight® 647 (Pierce); HiLyte Fluor™ 647, HiLyte Fluor™ 680, and HiLyte Fluor™ 750 (AnaSpec); IRDye® 800CW, IRDye® 800R5, and IRDye® 700DX (Li-Cor®); ADS780WS, ADS830WS, and ADS832WS (American Dye Source); XenoLight CF™ 680, XenoLight CF™ 750, XenoLight CF™ 770, and XenoLight DiR (Caliper® Life Sciences); and Kodak® X-SIGHT® 650, Kodak® X-SIGHT 691, Kodak® X-SIGHT 751 (Carestream® Health).

Suitable means for imaging, detecting, recording or measuring the present nanoparticles may also include, for example, a flow cytometer, a laser scanning cytometer, a fluorescence micro-plate reader, a fluorescence microscope, a confocal microscope, a bright-field microscope, a high content scanning system, and like devices. More than one imaging techniques may be used at the same time or consecutively to detect the present nanoparticles. In one embodiment, optical imaging is used as a sensitive, high-throughput screening tool to acquire multiple time points in the same subject, permitting semi-quantitative evaluations of tumor marker levels. This offsets the relatively decreased temporal resolution obtained with PET, although PET is needed to achieve adequate depth penetration for acquiring volumetric data, and to detect, quantitate, and monitor changes in receptor and/or other cellular marker levels as a means of assessing disease progression or improvement, as well as stratifying patients to suitable treatment protocols.

The systems and methods described herein can be used with other imaging approaches such as the use of devices including but not limited to various scopes (microscopes, endoscopes), catheters and optical imaging equipment, for example computer based hardware for tomographic presentations.

In certain embodiments, the systems and methods can be used in the detection, characterization and/or determination of the localization of a disease, especially early disease, the severity of a disease or a disease-associated condition, the staging of a disease, and monitoring and guiding various therapeutic interventions, such as surgical procedures, and monitoring and/or development of drug therapy and delivery, including cell based therapies. In certain embodiments, the methods can also be used in prognosis of a disease or disease condition.

In certain embodiments, the systems and methods described herein provide the ability to determine quantitative functional-metabolic multimodality particle-based imaging features that predict intratumoral distributions in high-grade gliomas. The provided systems and methods enable better stratification of patients suitable for particle-driven therapies and aid in better understanding cancer heterogeneity. Without wishing to be bound to any theory, radiomic analyses that combine structural, functional MM (e.g., perfusion, permeability, diffusion), and metabolic (PET) images can yield improved higher dimensional (e.g., 3D or 4D) data sets to better predict particle distributions in high grade gliomas than that derived from texture analysis alone.

The systems and methods described herein are not limited to IDH mutant gliomas and can be applied to various tumors with known or unknown genetic mutations. For example, the systems and methods described herein can be directed to any metastatic disease that goes to the brain (e.g., a glioma, e.g., a primary glioma, e.g., a low-grade glioma, e.g., a high-grade glioma).

In certain embodiments, the systems and methods described herein comprise investigating transgenic and conventional tumor models of primary and metastatic disease for detection and treatment using ultrasmall silica nanoparticles (e.g., nanoparticles having a diameter no greater than 20 nm, e.g. no greater than 15 nm, e.g., no greater than 10 nm. In certain embodiments, the systems and methods described herein comprise particle-driven regulation of the tumor microenvironment.

Constructive Example 1: Particle-Driven
Radiogenomics Determines Quantitative
Functional-Metabolic Multimodality Particle-Based
Imaging Features that Predicts Intratumoral and
Interstitial Nanoparticle Distributions in
High-Grade Gliomas The present Constructive Example provides the combination of particle-driven probes with texture analysis and functional and metabolic imaging. Various probes can be used. In preferred embodiments, the probes include nanoparticles (e.g., nanoparticles having a diameter no greater than 20 nm, no greater than 10 nm, e.g., C' dots).

The MRI and/or PET-CT scans of patients enrolled in particle-driven imaging studies can be examined. Features derived from images of subjects having particles administered thereto can be linked with particle tissue distributions to predict patient cohorts who may benefit from particle therapeutics as part of combination treatment paradigms (as described in Constructive Example 2).

The MRI and PET imaging scans of patients enrolled in particle imaging trials (n=10) and mutant IDH inhibitor trials at Memorial Sloan Kettering Cancer Center (n=18) can be examined. For example, computational tools such as a semi-automated and supervised image texture feature extraction can be used. These features are combined with functional and/or metabolic imaging tools to classify tumor physiology, metabolism, and composition, and also incorporate properties of the surrounding brain tumor parenchyma (e.g., presence/extent of edema) following systemic injection of clinically translated dual-modality cRGDY-PEG-C' dots.

Sample automated segmentation results based on structural images are illustrated in FIG. 1, and representative image-based features are shown in FIG. 2. FIG. 1 shows that a semi-automated confidence-based segmentation results in three different gliomas with corresponding confidence scores (red=higher, and blue=lower confidence). Experiments in 30 gliomas resulted in a segmentation accuracy of 0.8±0.1 (1=best segmentation). FIG. 2 shows exemplary images including textures, Gabor edges (at 4 different orientations), and textures on Gabor features that were computed on local patches to generate texture images in a glioma. Mean, kurtosis, and skewness summarized features such as Haralick textures (energy, entropy, correlation, homogeneity, contrast) and Haralick textures on Gabor edges (0°, 45°, 90°, 135°).

Alignment of all functional images and structural images can be performed using affine and deformable image registration methods (for example, as described in 3DSlicer (http://www.slicer.org/)).

The functional data can include, but is not limited to, diffusion-weighted imaging (DWI), diffusion tensor imaging (DTI), dynamic contrast enhanced (DCE) T1 perfusion imaging. In certain embodiments, custom software tools (e.g., those written in C++ and MATLAB) are used to automatically segment and then extract more than 256 image-based textures, Gabor edge features and Visually Accessible Rembrandt (VASARI) features.

In certain embodiments, the provided imaging features enable derivation of fingerprinting of molecular signatures combined with imaging features.

Constructive Example 2: Particle-Driven
Radiogenomics Identifies Quantitative Functional
MR Texture Features that can Predict Treatment
Efficacy in Low-Grade Gliomas Treated with
Mutation Specific Inhibitor In certain embodiments, particle-driven radiogenomics, for instance, as described in Constructive Example 1, extracts robust imaging features (e.g., from MRI and PET-CT scans of patients enrolled mutant IDH inhibitor trials (n=18 low grade glioma patients)) derived from particle probes administered to subjects.

In addition, imaging features extracted from small molecule inhibitor studies can be used to inform future particle-driven therapeutic trials. For example, when probes (e.g., molecular inhibitors (e.g., IDH)) are attached to nanoparticles administered to a subject, treatment efficacy of the particle probe can be determined for the subject on an individual basis. In certain embodiments, a probe comprises a therapeutic (e.g., a molecular inhibitor) in low grade glioma patients. In certain embodiments, probes are used as a baseline for therapeutics. In certain embodiments, particle probes comprise an RGD-based particle (e.g., cRGDY-PEG-C' dots). In certain embodiments, particle probes comprise nanoparticle drug conjugates.

Functional and/or structural imaging features that predict treatment efficacy can also be evaluated following inhibitor therapy, and can be correlated with patient outcomes such as progression-free survival and overall survival.

In certain embodiments, the systems and methods described herein identify quantitative functional magnetic resonance (MR) texture features that can predict treatment efficacy in low-grade gliomas treated with mutation specific inhibitor therapy. Without wishing to be bound to any theory, radiomic analyses of MR diffusion and perfusion functional images provide high-dimensional data (e.g., 3D or 4D data) to better predict inhibitor treatment efficacy in, for example, IDH mutant gliomas, compared to structural images alone.

Specific imaging features, in addition to genetic mutations and disease history, can be used to better stratify patients to appropriate treatment arms that may incorporate nanoparticle drug conjugates (NDCs) as part of a combinatorial strategy.

Constructive Example 3: MR Vascular Signature

Multi-modal, multi-parametric, quantitative imaging datasets gleaned from functional radiodiagnosis technologies and genomics in conjunction with or without imaging tracer probes (e.g., ultrasmall nanoparticles) can be interfaced with derived knowledge bases to improve diagnostic and/or theranostic accuracy and predictive power for clinical decision support systems. As provided herein, high-throughput extraction of quantitative imaging features and data standardization and curation can be converted to mineable data for combined readouts. These multidimensional sub-volume data sets are modeled and embedded with pattern recognition tools for advanced analytics and visualization.

Tumor vasculature is highly complex and chaotically organized; an assessment of heterogeneity and its aggressiveness in the tumor regions (e.g., hyper/hypo/low) are considered to be of paramount clinical significance in cancer therapy. In-vivo MR imaging biomarkers can play an important role in prognosis, monitoring target therapy response and a future epitome in personalized medicine. To this end, provided herein are systems and methods of pattern recognition (e.g., MR Vasculature Signature) to evaluate the glioma heterogeneity and aggressiveness.

Advances in medical image post processing methods often involve image segmentation and threshold techniques in the image space read out. The development of a MR Vasculature Signature algorithm is based on the postulates that intra-class objects in any heterogeneity region manifest themselves fuzzy boundaries. In order to differentiate between boundaries, an image morphological property based on the histogram analyzes of intra-class variances and region homogeneity was formulated to determine the multi-level overall minimizing energy criteria for characterization. Further, a standard computation on the number of interface junctions inside the tumor region can provide accurate hemodynamic metrics in comparison with contralateral. The superiority and robustness of the disclosed systems and methods can be observed both qualitatively as well as quantitatively on a generated cerebral blood flow map and is faster employing custom developed software. The provided systems and methods also help to facilitate delineation of the necrotic area and detect angiogenic hotspots even in non-enhancement within the tumor as well as to classify tumor.

As tumor size progress, the vascularization increases correspondingly. Given the degree of heterogeneity of tumors and proliferations, the provided systems and methods such as the MR Vasculature Signature method indicates the scale of aggressiveness and may serve as a surrogate image biomarker in evaluation of the severity and to identify the extent of aggressiveness. This would further help to detect molecular correlates reflecting the biological status of tumors, which, in turn can direct target therapies and may provide distinguished profile to potentiate personalized care.

FIG. 5 shows multimodal multi-parametric maps (e.g., PET/CT, DCE-MRI, MRI) for physiological quantitative metrics.

FIG. 6A shows cerebral blood flow (CBF) maps P1.

FIG. 6B shows vascular signatures corresponding to CBF maps P1.

FIG. 7A shows cerebral blood flow maps P2.

FIG. 7B shows vascular signatures corresponding to CBF maps P2.

Constructive Example 4: Integration of Clinical Imaging Readouts and Analyses of High Dimensional Data Tracer kinetics facilitate exploration of in vivo imaging strategies and computationally-intensive approaches to address the fundamental biological process at molecular and/or cellular levels and also to improve in vivo assessment methods for real-time surgical, image-guided target interventions, diagnosis, and therapy towards unmet clinical challenges.

Various factors (e.g., size, characterization, architecture, composition, concentration, dose, uptake, binding, uptake, delivery properties, cellular internalization, metabolic profiles, phenotype, activatable and/or inhibitory profile of gene-based multimodal probes) of particle-driven tracer kinetics have also fueled paradigm shift in exploitation of image contrast mechanisms and signal and image processing techniques for enhanced intensity profiles of measurable signal(s) (e.g., signal to noise ratio (SNR), contrast to noise ratio (CNR)) and physiological quantitative accuracies (FIG. 8).

By integrating clinical imaging readouts with acquisition, the complex analyses of high dimensional data are classified and/or clustered through generation of application-based imaging pipelines and clinical work flow optimization. The classification and/or clustering can be based on alterations in tissue characterization, oncometabolites, molecular events and/or alterations in cellular profile (e.g., epigenetic, inhibition and/or initiation of tumorigenesis). Through processing unit(s) and/or module(s), a plurality (e.g., hundreds) of imaging features (including but not limited to texture properties) and parametric values are derived and correlated.

Knowledge-based imaging database libraries are developed for linking the functional information with a priori knowledge. Also, during the data standardization and curation, the Modeler unit buildup identifies molecular signatures (e.g., hypoxia, angiogenesis, transcriptome, vessel index, vasculature). Subsequently, pattern recognitions tools (e.g., matrices including the imaging features based on clinical conditions and/or metrics) can be generated for computational stratification of preoperative and intraoperative imaging features (e.g., wherein the features are suspected, targeted, and/or screening) of brain tumor patients.

FIG. 3 shows an illustrative network environment 300 for use in the methods and systems for analysis of spectrometry data corresponding to particles of a sample, as described herein. In brief overview, referring now to FIG. 3, a block diagram of an exemplary cloud computing environment 300 is shown and described. The cloud computing environment 300 may include one or more resource providers 302a, 302b, 302c (collectively, 302). Each resource provider 302 may include computing resources. In some implementations, computing resources may include any hardware and/or software used to process data. For example, computing resources may include hardware and/or software capable of executing algorithms, computer programs, and/or computer applications. In some implementations, exemplary computing resources may include application servers and/or databases with storage and retrieval capabilities. Each resource provider 302 may be connected to any other resource provider 302 in the cloud computing environment 300. In some implementations, the resource providers 302 may be connected over a computer network 308. Each resource provider 302 may be connected to one or more computing device 304a, 304b, 304c (collectively, 304), over the computer network 308.

The cloud computing environment 300 may include a resource manager 306. The resource manager 306 may be connected to the resource providers 302 and the computing devices 304 over the computer network 308. In some implementations, the resource manager 306 may facilitate the provision of computing resources by one or more resource providers 302 to one or more computing devices 304. The resource manager 306 may receive a request for a computing resource from a particular computing device 304. The resource manager 306 may identify one or more resource providers 302 capable of providing the computing resource requested by the computing device 304. The resource manager 306 may select a resource provider 302 to provide the computing resource. The resource manager 306 may facilitate a connection between the resource provider 302 and a particular computing device 304. In some implementations, the resource manager 306 may establish a connection between a particular resource provider 302 and a particular computing device 304. In some implementations, the resource manager 306 may redirect a particular computing device 304 to a particular resource provider 302 with the requested computing resource.

FIG. 4 shows an example of a computing device 400 and a mobile computing device 450 that can be used in the methods and systems described in this disclosure. The computing device 400 is intended to represent various forms of digital computers, such as laptops, desktops, workstations, personal digital assistants, servers, blade servers, mainframes, and other appropriate computers. The mobile computing device 450 is intended to represent various forms of mobile devices, such as personal digital assistants, cellular telephones, smart-phones, and other similar computing devices. The components shown here, their connections and relationships, and their functions, are meant to be examples only, and are not meant to be limiting.

The computing device 400 includes a processor 402, a memory 404, a storage device 406, a high-speed interface 408 connecting to the memory 404 and multiple high-speed expansion ports 410, and a low-speed interface 412 connecting to a low-speed expansion port 414 and the storage device 406. Each of the processor 402, the memory 404, the storage device 406, the high-speed interface 408, the high-speed expansion ports 410, and the low-speed interface 412, are interconnected using various busses, and may be mounted on a common motherboard or in other manners as appropriate. The processor 402 can process instructions for execution within the computing device 400, including instructions stored in the memory 404 or on the storage device 406 to display graphical information for a GUI on an external input/output device, such as a display 416 coupled to the high-speed interface 408. In other implementations, multiple processors and/or multiple buses may be used, as appropriate, along with multiple memories and types of memory. Also, multiple computing devices may be connected, with each device providing portions of the necessary operations (e.g., as a server bank, a group of blade servers, or a multi-processor system).

The memory 404 stores information within the computing device 400. In some implementations, the memory 404 is a volatile memory unit or units. In some implementations, the memory 404 is a non-volatile memory unit or units. The memory 404 may also be another form of computer-readable medium, such as a magnetic or optical disk.

The storage device 406 is capable of providing mass storage for the computing device 400. In some implementations, the storage device 406 may be or contain a computer-readable medium, such as a floppy disk device, a hard disk device, an optical disk device, or a tape device, a flash memory or other similar solid state memory device, or an array of devices, including devices in a storage area network or other configurations. Instructions can be stored in an information carrier. The instructions, when executed by one or more processing devices (for example, processor 402), perform one or more methods, such as those described above. The instructions can also be stored by one or more storage devices such as computer- or machine-readable mediums (for example, the memory 404, the storage device 406, or memory on the processor 402).

The high-speed interface 408 manages bandwidth-intensive operations for the computing device 400, while the low-speed interface 412 manages lower bandwidth-intensive operations. Such allocation of functions is an example only. In some implementations, the high-speed interface 408 is coupled to the memory 404, the display 416 (e.g., through a graphics processor or accelerator), and to the high-speed expansion ports 410, which may accept various expansion cards (not shown). In the implementation, the low-speed interface 412 is coupled to the storage device 406 and the low-speed expansion port 414. The low-speed expansion port 414, which may include various communication ports (e.g., USB, Bluetooth®, Ethernet, wireless Ethernet) may be coupled to one or more input/output devices, such as a keyboard, a pointing device, a scanner, or a networking device such as a switch or router, e.g., through a network adapter.

The computing device 400 may be implemented in a number of different forms, as shown in the figure. For example, it may be implemented as a standard server 420, or multiple times in a group of such servers. In addition, it may be implemented in a personal computer such as a laptop computer 422. It may also be implemented as part of a rack server system 424. Alternatively, components from the computing device 400 may be combined with other components in a mobile device (not shown), such as a mobile computing device 450. Each of such devices may contain one or more of the computing device 400 and the mobile computing device 450, and an entire system may be made up of multiple computing devices communicating with each other.

The mobile computing device 450 includes a processor 452, a memory 464, an input/output device such as a display 454, a communication interface 466, and a transceiver 468, among other components. The mobile computing device 450 may also be provided with a storage device, such as a micro-drive or other device, to provide additional storage. Each of the processor 452, the memory 464, the display 454, the communication interface 466, and the transceiver 468, are interconnected using various buses, and several of the components may be mounted on a common motherboard or in other manners as appropriate.

The processor 452 can execute instructions within the mobile computing device 450, including instructions stored in the memory 464. The processor 452 may be implemented as a chipset of chips that include separate and multiple analog and digital processors. The processor 452 may provide, for example, for coordination of the other components of the mobile computing device 450, such as control of user interfaces, applications run by the mobile computing device 450, and wireless communication by the mobile computing device 450.

The processor 452 may communicate with a user through a control interface 458 and a display interface 456 coupled to the display 454. The display 454 may be, for example, a TFT (Thin-Film-Transistor Liquid Crystal Display) display or an OLED (Organic Light Emitting Diode) display, or other appropriate display technology. The display interface 456 may comprise appropriate circuitry for driving the display 454 to present graphical and other information to a user. The control interface 458 may receive commands from a user and convert them for submission to the processor 452. In addition, an external interface 462 may provide communication with the processor 452, so as to enable near area communication of the mobile computing device 450 with other devices. The external interface 462 may provide, for example, for wired communication in some implementations, or for wireless communication in other implementations, and multiple interfaces may also be used.

The memory 464 stores information within the mobile computing device 450. The memory 464 can be implemented as one or more of a computer-readable medium or media, a volatile memory unit or units, or a non-volatile memory unit or units. An expansion memory 474 may also be provided and connected to the mobile computing device 450 through an expansion interface 472, which may include, for example, a SIMM (Single In Line Memory Module) card interface. The expansion memory 474 may provide extra storage space for the mobile computing device 450, or may also store applications or other information for the mobile computing device 450. Specifically, the expansion memory 474 may include instructions to carry out or supplement the processes described above, and may include secure information also. Thus, for example, the expansion memory 474 may be provided as a security module for the mobile computing device 450, and may be programmed with instructions that permit secure use of the mobile computing device 450. In addition, secure applications may be provided via the SIMM cards, along with additional information, such as placing identifying information on the SIMM card in a non-hackable manner.

The memory may include, for example, flash memory and/or NVRAM memory (non-volatile random access memory), as discussed below. In some implementations, instructions are stored in an information carrier and, when executed by one or more processing devices (for example, processor 452), perform one or more methods, such as those described above. The instructions can also be stored by one or more storage devices, such as one or more computer- or machine-readable mediums (for example, the memory 464, the expansion memory 474, or memory on the processor 452). In some implementations, the instructions can be received in a propagated signal, for example, over the transceiver 468 or the external interface 462.

The mobile computing device 450 may communicate wirelessly through the communication interface 466, which may include digital signal processing circuitry where necessary. The communication interface 466 may provide for communications under various modes or protocols, such as GSM voice calls (Global System for Mobile communications), SMS (Short Message Service), EMS (Enhanced Messaging Service), or MMS messaging (Multimedia Messaging Service), CDMA (code division multiple access), TDMA (time division multiple access), PDC (Personal Digital Cellular), WCDMA (Wideband Code Division Multiple Access), CDMA2000, or GPRS (General Packet Radio Service), among others. Such communication may occur, for example, through the transceiver 468 using a radio-frequency. In addition, short-range communication may occur, such as using a Bluetooth®, Wi-Fi™, or other such transceiver (not shown). In addition, a GPS (Global Positioning System) receiver module 470 may provide additional navigation- and location-related wireless data to the mobile computing device 450, which may be used as appropriate by applications running on the mobile computing device 450.

The mobile computing device 450 may also communicate audibly using an audio codec 460, which may receive spoken information from a user and convert it to usable digital information. The audio codec 460 may likewise generate audible sound for a user, such as through a speaker, e.g., in a handset of the mobile computing device 450. Such sound may include sound from voice telephone calls, may include recorded sound (e.g., voice messages, music files, etc.) and may also include sound generated by applications operating on the mobile computing device 450.

The mobile computing device 450 may be implemented in a number of different forms, as shown in the figure. For example, it may be implemented as a cellular telephone 480. It may also be implemented as part of a smart-phone 482, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms machine-readable medium and computer-readable medium refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term machine-readable signal refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network (LAN), a wide area network (WAN), and the Internet.

The computing system can include clients and servers. A client and server are generally remote from each other and typically interact through a communication network. The relationship of client and server arises by virtue of computer programs running on the respective computers and having a client-server relationship to each other.

What is claimed is:

1. An in vivo method for determining an intratumoral and/or interstitial nanoparticle distribution within a tumor and/or a tumor interstitium of a subject, the method comprising the steps of:

administering to the subject a single probe species that consists of a plurality of individual silica-based nanoparticles of the same species;

following the administering step, obtaining a plurality of in vivo images of the subject;

producing, by a processor of a computing device, one or more segments from at least one of the plurality of in vivo images;

extracting, by the processor, one or more features from at least one of the one or more segments;

accessing, by the processor, functional and/or metabolic imaging data from at least one of the plurality of in vivo images and extracting and combining quantitative multi-dimensional data generated from the functional and/or metabolic imaging data; and determining the intratumoral and/or interstitial nanoparticle distribution within the tumor and/or the tumor interstitium of the subject using the extracted one or more features and the accessed functional and/or metabolic imaging data.

2. The method of claim 1, wherein the tumor comprises a metastatic disease, and wherein the metastasis is in the brain.

3. The method of claim 1, wherein the tumor comprises a primary glioma.

4. The method of claim 1, wherein the tumor comprises a low-grade glioma or high-grade glioma.

5. The method of claim 1, wherein the nanoparticles have an average diameter no greater than 20 nm.

6. The method of claim 1, wherein a radioisotope is attached directly or indirectly to each nanoparticle.

7. The method of claim 1, wherein a therapeutic is attached directly or indirectly to each nanoparticle.

8. The method of claim 1, wherein the plurality of in vivo images comprises a member selected from the group consisting of a positron emission tomography (PET) images(s), X-ray images(s), magnetic resonance imaging (MRI) images(s), Computed Tomography (CT) images(s), Single-Photon Emission Computed Tomography (SPECT) images(s), PET-CT images(s), and ultrasound image(s).

9. The method of claim 1, wherein the plurality of in vivo images comprises a combination of two or more of PET images(s), X-ray images(s), MRI images(s), CT images(s), SPECT images(s), PET-CT images(s), and ultrasound image(s).

10. The method of claim 1, wherein the one or more features are one or more texture features comprising Gabor edge features and/or Visually Accessible Rembrandt features.

11. The method of claim 1, wherein the functional and/or metabolic imaging data comprises one or more of the following: diffusion-weighted imaging data, diffusion tensor imaging data, and/or dynamic contrast enhanced T1 perfusion imaging data.

12. A system comprising:

a single probe species that consists of a plurality of individual silica-based nanoparticles of the same species;

one or more imaging devices;

a processor; and a nontransitory computer readable medium having instructions stored thereon, wherein the instructions, when executed by the processor, cause the processor to:

(i) produce one or more segments from at least one of a plurality of in vivo images obtained using the one or more imaging devices;

(ii) extract one or more features from at least one of the one or more segments;

(iii) access functional and/or metabolic imaging data from at least one of the plurality of in vivo images, and extract and combine quantitative multi-dimensional data generated from the functional and/or metabolic imaging data;

(iv) determine an intratumoral and/or interstitial nanoparticle distribution within a tumor and/or a tumor interstitium of a subject using the extracted one or more features and the accessed functional and/or metabolic imaging data; and (v) link the determined intratumoral and/or interstitial silica based nanoparticle distribution within the tumor interstitium to the extracted and combined multi-dimensional data; and (vi) cause display of a graphical representation of the intratumoral and/or interstitial nanoparticle distribution within the tumor and/or the tumor interstitium superimposed on an image of the tumor and/or tumor interstitium captured by the one or more imaging devices.

13. The system of claim 12, wherein the one or more features are one or more texture features, and wherein the one or more texture features comprise Gabor edge features and/or Visually Accessible Rembrandt features.

14. The system of claim 12, wherein the functional and/or metabolic imaging data comprises one or more of the following: diffusion-weighted imaging data, diffusion tensor imaging data, and/or dynamic contrast enhanced T1 perfusion imaging data.

15. The system of claim 12, wherein the instructions further cause the processor to determine a measure of treatment efficacy using the extracted one or more features.

16. The system of claim 15, wherein the one or more features are functional and/or structural features.

17. The system of claim 12, wherein the instructions cause the processor to extract one or more features by identifying quantitative functional magnetic resonance (MR) texture features.

18. The system of claim 12, wherein a molecular inhibitor is attached directly or indirectly to each nanoparticle.

19. The system of claim 15, wherein the instructions cause the processor to determine the measure of treatment efficacy using high-dimensional data from one or more radiomic analysis of MR diffusion and/or perfusion functional images to predict inhibitor treatment efficacy.

20. The system of claim 15, wherein the instructions, when executed by the processor, further cause the processor to determine a measure of glioma heterogeneity using the extracted one or more features.

21. The system of claim 12, wherein step (i) comprises determining a multi-level overall minimizing energy criteria for characterization.

22. The system of claim 20, wherein the instructions cause the processor to determine a measure of glioma heterogeneity by determining hemodynamic metrics using a computation of the number of interface junctions inside a tumor region, and/or determining an MR vascular signature.

23. The system of claim 12, wherein the nanoparticles have an average diameter no greater than 20 nm.

24. The system of claim 23, wherein the nanoparticles have an average diameter no greater than 10 nm.

25. The system of claim 12, wherein a therapeutic is attached directly or indirectly to each nanoparticle.

26. The system of claim 12, wherein a radioisotope is attached directly or indirectly to each nanoparticle.

27. The system of claim 12, wherein each nanoparticle is a dual-modality cRGDY-PEG-C dot.

28. The system of claim 12, wherein the one or more imaging devices is selected from MR, PET, SPECT, CT, ultrasound, X-ray, and a combination thereof.

29. The system of claim 15, wherein a molecular inhibitor is attached to each nanoparticle and wherein the measure is a prediction of treatment efficacy in a low-grade glioma treated with the mutation specific inhibitor therapy.

30. The system of claim 16, wherein the features comprise quantitative functional magnetic resonance (MR) texture features.

31. The system of claim 15, wherein the instructions cause the processor to determine the measure of treatment efficacy using the extracted one or more features in addition to data regarding genetic mutations and/or disease history of the subject.

32. The method of claim 1, further comprising linking the determined intratumoral and/or interstitial nanoparticle distribution within the tumor and/or the tumor interstitium to the extracted and combined multi-dimensional data; and causing a display of a graphical representation of the intratumoral and/or interstitial nanoparticle distribution within the tumor and/or the tumor interstitium superimposed on an image of the tumor and/or tumor interstitium.

33. The method of claim 1, wherein the one or more features are one or more texture features comprising Gabor edge features; and wherein the tumor comprises a primary glioma.

34. The system of claim 12, wherein the one or more features are one or more texture features comprising Gabor edge features; and wherein the tumor comprises a primary glioma.

\* \* \* \* \*